United States Patent
Castro et al.

(10) Patent No.: US 10,004,731 B2
(45) Date of Patent: *Jun. 26, 2018

(54) FLIBANSERIN FOR THE TREATMENT OF URINARY INCONTINENCE AND RELATED DISEASES

(71) Applicant: Sprout Pharmaceuticals, Inc., Bridgewater, NJ (US)

(72) Inventors: Ramiro Castro, Bryn Mawr, PA (US); Angelo Ceci, Mittelbiberach (DE)

(*) Notice: Subject to any disclaimer, the term of this patent is extended or adjusted under 35 U.S.C. 154(b) by 0 days. days.

This patent is subject to a terminal disclaimer.

(21) Appl. No.: 15/686,383

(22) Filed: Aug. 25, 2017

(65) Prior Publication Data

US 2018/0071282 A1 Mar. 15, 2018

Related U.S. Application Data

(63) Continuation of application No. 14/809,862, filed on Jul. 27, 2015, now Pat. No. 9,763,936, which is a continuation of application No. 13/680,722, filed on Nov. 19, 2012, now abandoned, which is a continuation of application No. 12/306,878, filed as application No. PCT/EP2007/056400 on Jun. 27, 2007, now abandoned.

(30) Foreign Application Priority Data

Jun. 30, 2006 (EP) .................... 06116393

(51) Int. Cl.
| | | |
|---|---|---|
| A61K 38/00 | (2006.01) | |
| A61K 31/496 | (2006.01) | |
| A61K 31/137 | (2006.01) | |
| A61K 45/06 | (2006.01) | |
| A61K 31/381 | (2006.01) | |
| A61K 31/138 | (2006.01) | |
| A61K 38/11 | (2006.01) | |
| A61K 38/22 | (2006.01) | |

(52) U.S. Cl.
CPC .......... *A61K 31/496* (2013.01); *A61K 31/137* (2013.01); *A61K 31/138* (2013.01); *A61K 31/381* (2013.01); *A61K 38/11* (2013.01); *A61K 38/22* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,096,248 A | 7/1963 | Rudzki | |
| 3,406,178 A | 10/1968 | Crocker et al. | |
| 3,472,854 A | 10/1969 | Archer | |
| 4,200,641 A | 4/1980 | Vandenberk et al. | |
| 4,367,217 A | 1/1983 | Gruber et al. | |
| 4,438,091 A | 3/1984 | Gruber et al. | |
| 4,737,500 A | 4/1988 | Sorg | |
| 4,792,452 A | 12/1988 | Howard et al. | |
| 4,797,399 A | 1/1989 | Ueda et al. | |
| 4,859,692 A | 8/1989 | Bernstein et al. | |
| 4,886,803 A | 12/1989 | Sueda et al. | |
| 4,940,793 A | 7/1990 | Botre et al. | |
| 4,954,503 A | 9/1990 | Strupczewski et al. | |
| 4,968,508 A | 11/1990 | Oren et al. | |
| 5,002,948 A | 3/1991 | Perregaard et al. | |
| 5,036,088 A | 7/1991 | Kitaura et al. | |
| 5,225,417 A | 7/1993 | Dappen et al. | |
| 5,281,585 A | 1/1994 | Duggan et al. | |
| 5,405,642 A | 4/1995 | Gilis et al. | |
| 5,407,686 A | 4/1995 | Patel et al. | |
| 5,434,156 A | 7/1995 | Bjork et al. | |
| 5,482,948 A | 1/1996 | Soyka et al. | |
| 5,492,907 A | 2/1996 | Pickar et al. | |
| 5,552,412 A | 9/1996 | Cameron et al. | |
| 5,576,290 A | 11/1996 | Hadley | |
| 5,576,318 A | 11/1996 | Bietti et al. | |
| 5,591,743 A | 1/1997 | Patoiseau et al. | |
| 5,854,290 A | 12/1998 | Arnsten et al. | |
| 5,883,094 A | 3/1999 | Fliri et al. | |
| 5,916,916 A | 6/1999 | Hauser et al. | |
| 5,929,054 A | 7/1999 | Baker et al. | |
| 5,977,106 A | 11/1999 | Patoiseau et al. | |
| 6,051,555 A | 4/2000 | Hadley | |
| 6,068,846 A | 5/2000 | Cho et al. | |
| 6,083,947 A | 7/2000 | Granger et al. | |
| 6,165,513 A | 12/2000 | Dansereau et al. | |

(Continued)

FOREIGN PATENT DOCUMENTS

| | | |
|---|---|---|
| BE | 904945 | 12/1986 |
| CA | 2455628 | 2/2003 |

(Continued)

OTHER PUBLICATIONS

Berge et al., Pharmaceutical Salts, J Pharm Sci., 1977, 66(1):1-19.
Kumar et al., An Overview of Automated Systems Relevant in Pharmaceutical Salt Screening; Drug Discovery Today, 2007, 12(23-24):1046-1053.
Stahl et al., Handbook of Pharmaceutical Salts: Selection and Use, Helvetica Chim. Acta, 2002, pp. 1-7.
U.S. Appl. No. 13/131,926, filed May 31, 2011, Mazurek et al.
Eriksson, Serotonin reuptake inhibitors for the treatment of premenstrual dysphoria, Intl. Clin. Psychopharm, 1999, 14Supp2:S27-S33.
Steiner et al., Seretonin re-uptake inhibitors in the treatment of premenstrual dysphoria: Current status of knowledge, 1997, 1:241-247.

(Continued)

*Primary Examiner* — Jeanette M Lieb
(74) *Attorney, Agent, or Firm* — Parker Poe Adams & Bernstein LLP

(57) ABSTRACT

The invention relates to the use of Flibanserin for the treatment or prevention of urinary incontinence and related diseases. In a further embodiment, the instant invention is directed to pharmaceutical combinations comprising flibanserin as one active ingredient in combination with at least one additional active ingredient for the treatment or prevention of urinary incontinence and related diseases.

17 Claims, No Drawings

(56) References Cited

U.S. PATENT DOCUMENTS

| | | |
|---|---|---|
| 6,187,340 B1 | 2/2001 | Fukuta et al. |
| 6,281,218 B1 | 8/2001 | Cereda et al. |
| 6,284,757 B1 | 9/2001 | Sanner |
| 6,346,548 B1 | 2/2002 | Miller et al. |
| 6,426,087 B1 | 7/2002 | Saslawski et al. |
| 6,482,841 B1 | 11/2002 | Letelier et al. |
| 6,521,623 B1 | 2/2003 | Cereda et al. |
| 6,586,435 B2 | 7/2003 | Cereda et al. |
| 6,627,646 B2 | 9/2003 | Bakale et al. |
| 6,680,071 B1 | 1/2004 | Johnson et al. |
| 7,151,103 B2 | 12/2006 | Borsini et al. |
| 7,183,410 B2 | 2/2007 | Bombarda et al. |
| 7,241,805 B2 | 7/2007 | Oberegger et al. |
| 7,420,057 B2 | 9/2008 | Bombarda et al. |
| 7,973,043 B2 | 7/2011 | Migaly |
| 8,030,314 B2 | 10/2011 | Beck |
| 8,545,886 B2 | 10/2013 | Eisenreich et al. |
| 8,658,207 B2 | 2/2014 | Eisenreich et al. |
| 8,722,682 B2 | 5/2014 | Volz et al. |
| 8,785,458 B2 | 7/2014 | Ceci et al. |
| 2002/0001397 A1 | 1/2002 | Ishikawa et al. |
| 2002/0010216 A1 | 1/2002 | Rogosky et al. |
| 2002/0052370 A1 | 5/2002 | Barber et al. |
| 2002/0091115 A1 | 7/2002 | Dyatkin et al. |
| 2002/0103208 A1 | 8/2002 | Cereda et al. |
| 2002/0151543 A1 | 10/2002 | Barberish et al. |
| 2003/0027823 A1 | 2/2003 | Cereda et al. |
| 2003/0055070 A1 | 3/2003 | Harrison et al. |
| 2003/0060475 A1 | 3/2003 | Borsini |
| 2003/0083228 A1 | 5/2003 | Carpino et al. |
| 2003/0104980 A1 | 6/2003 | Borsini et al. |
| 2003/0119850 A1 | 6/2003 | Bombarda et al. |
| 2004/0023948 A1 | 2/2004 | Green et al. |
| 2004/0048877 A1 | 3/2004 | Friedl et al. |
| 2004/0116532 A1 | 6/2004 | Heacock et al. |
| 2004/0132697 A1 | 7/2004 | Thurlow et al. |
| 2004/0147581 A1 | 7/2004 | Taylor et al. |
| 2004/0180904 A1 | 9/2004 | Beck |
| 2004/0193452 A1 | 9/2004 | Berman |
| 2004/0198706 A1 | 10/2004 | Carrara et al. |
| 2004/0235861 A1 | 11/2004 | Borsini |
| 2004/0258749 A1 | 12/2004 | Guldner et al. |
| 2005/0004105 A1 | 1/2005 | Leahy et al. |
| 2005/0037983 A1 | 2/2005 | Dinan et al. |
| 2005/0065158 A1 | 3/2005 | Naylor et al. |
| 2005/0090550 A1 | 4/2005 | Barrett |
| 2005/0095293 A1 | 5/2005 | Brauns et al. |
| 2005/0159430 A1 | 7/2005 | Bombarda et al. |
| 2005/0239798 A1 | 10/2005 | Pyke |
| 2005/0245539 A1 | 11/2005 | Mendla et al. |
| 2006/0014757 A1 | 1/2006 | Pyke |
| 2006/0025420 A1 | 2/2006 | Brauns et al. |
| 2006/0052391 A1 | 3/2006 | Dolsten |
| 2006/0084700 A1 | 4/2006 | Michel |
| 2006/0160822 A1 | 7/2006 | Borsini |
| 2006/0199805 A1 | 9/2006 | Pyke et al. |
| 2006/0204486 A1 | 9/2006 | Pyke et al. |
| 2006/0211685 A1 | 9/2006 | Pyke et al. |
| 2006/0252773 A1 | 11/2006 | Ceci et al. |
| 2006/0258640 A1 | 11/2006 | Ceci et al. |
| 2006/0264511 A1 | 11/2006 | Pyke |
| 2006/0264512 A1 | 11/2006 | Pyke |
| 2007/0032654 A1 | 2/2007 | Bombarda et al. |
| 2007/0032655 A1 | 2/2007 | Bombarda et al. |
| 2007/0072872 A1 | 3/2007 | Borsini et al. |
| 2007/0105869 A1 | 5/2007 | Pollentier et al. |
| 2007/0123540 A1 | 5/2007 | Ceci |
| 2007/0196473 A1 | 8/2007 | Friedl et al. |
| 2007/0265276 A1 | 11/2007 | Pollentier et al. |
| 2008/0038346 A1 | 2/2008 | Eisenreich et al. |
| 2008/0038347 A1 | 2/2008 | Eisenreich et al. |
| 2008/0069873 A1 | 3/2008 | Pearnchob et al. |
| 2008/0103155 A1 | 5/2008 | Mendla et al. |
| 2008/0119482 A1 | 5/2008 | Dolsten |
| 2008/0242678 A1 | 10/2008 | Ceci et al. |
| 2008/0242679 A1 | 10/2008 | Ceci |
| 2009/0023712 A1 | 1/2009 | Ferger et al. |
| 2009/0054458 A1 | 2/2009 | Bombarda et al. |
| 2009/0176698 A1 | 7/2009 | Baiker et al. |
| 2009/0239881 A1 | 9/2009 | Becker |
| 2009/0247546 A1 | 10/2009 | Ceci et al. |
| 2009/0312242 A1 | 12/2009 | Castrol et al. |
| 2009/0318469 A1 | 12/2009 | Pyke et al. |
| 2013/0172304 A1 | 7/2013 | Boeck |
| 2013/0203671 A1 | 8/2013 | Castro et al. |
| 2013/0203766 A1 | 8/2013 | Mendla et al. |

FOREIGN PATENT DOCUMENTS

| | | |
|---|---|---|
| CA | 2 515 426 C | 1/2012 |
| CL | 1033-1999 | 5/1999 |
| CL | 2394-1999 | 10/1999 |
| CL | 1491-2001 | 6/2001 |
| CL | 2833-2001 | 11/2001 |
| CL | 418-2002 | 3/2002 |
| CL | 1706-2002 | 7/2002 |
| CL | 1878-2002 | 8/2002 |
| CL | 2389-2002 | 10/2002 |
| CL | 1751-2004 | 7/2004 |
| CL | 911-2005 | 4/2005 |
| CN | 1571670 A | 1/2005 |
| CN | 1655789 A | 8/2005 |
| DE | 3620643 | 1/1987 |
| DE | 10209982.0 | 3/2002 |
| DE | 10138273 | 2/2003 |
| EP | 0200322 | 11/1986 |
| EP | 0376607 | 7/1990 |
| EP | 0497985 | 8/1992 |
| EP | 0526434 | 2/1993 |
| EP | 0547517 A1 | 6/1993 |
| EP | 0705832 | 4/1996 |
| EP | 0816356 | 1/1998 |
| EP | 0982030 | 3/2000 |
| EP | 1256343 | 11/2002 |
| EP | 1285658 | 2/2003 |
| EP | 1014985 | 5/2003 |
| EP | 1518858 | 3/2005 |
| EP | 1674102 | 6/2006 |
| GB | 2023594 | 1/1980 |
| IE | 19921340 | 10/1992 |
| IL | 159151 | 2/2003 |
| IL | 160389 | 2/2004 |
| JP | 58134033 | 8/1983 |
| JP | 8143476 | 6/1996 |
| RU | 93014306 A | 3/1995 |
| WO | WO 1992002215 A1 | 8/1991 |
| WO | WO 199203167 A1 | 3/1992 |
| WO | WO 199219606 A1 | 11/1992 |
| WO | WO 1993003016 A1 | 2/1993 |
| WO | WO 1995001965 A1 | 1/1995 |
| WO | WO 1995/19978 A1 | 7/1995 |
| WO | WO 1995034555 A1 | 12/1995 |
| WO | WO 1996005834 A1 | 2/1996 |
| WO | WO 1996016949 A1 | 6/1996 |
| WO | 98/19668 A1 | 5/1998 |
| WO | WO 1998019668 A1 | 5/1998 |
| WO | WO 1998033784 A1 | 8/1998 |
| WO | WO 1998042344 A1 | 10/1998 |
| WO | WO 1999019302 A1 | 4/1999 |
| WO | WO 1999059593 A1 | 5/1999 |
| WO | WO 1999/59584 A1 | 11/1999 |
| WO | 99/064002 A1 | 12/1999 |
| WO | WO 2000/24383 A1 | 5/2000 |
| WO | WO 2000028993 A1 | 5/2000 |
| WO | WO 2000/63193 A1 | 10/2000 |
| WO | WO 2000/67735 A2 | 11/2000 |
| WO | WO 2000064441 A2 | 11/2000 |
| WO | WO 2001/00224 A1 | 1/2001 |
| WO | WO 2001012170 A2 | 2/2001 |
| WO | WO 2001021593 A1 | 3/2001 |
| WO | WO 2002/00654 A1 | 1/2002 |
| WO | WO 2002024662 A1 | 3/2002 |
| WO | WO 2002/41894 A2 | 5/2002 |
| WO | 02/072586 A1 | 9/2002 |

(56) References Cited

FOREIGN PATENT DOCUMENTS

| WO | 02/074288 A2 | 9/2002 |
|---|---|---|
| WO | WO 2002/72586 A1 | 9/2002 |
| WO | WO 2002079143 A1 | 10/2002 |
| WO | WO 2003/07949 A1 | 1/2003 |
| WO | WO 2003011396 A1 | 2/2003 |
| WO | WO 2003013539 A1 | 2/2003 |
| WO | WO 2003014079 A1 | 2/2003 |
| WO | 03/030869 A1 | 4/2003 |
| WO | WO 2003035072 A1 | 5/2003 |
| WO | WO 2003074032 A1 | 9/2003 |
| WO | WO 2003097058 A1 | 11/2003 |
| WO | WO 2004041259 A1 | 5/2004 |
| WO | WO 2004045509 A2 | 6/2004 |
| WO | WO 2004069339 A1 | 8/2004 |
| WO | WO 2005/07166 A1 | 1/2005 |
| WO | WO 2005044238 A1 | 5/2005 |
| WO | WO 2005087207 A1 | 9/2005 |
| WO | WO 2005102342 A1 | 11/2005 |
| WO | WO 2005102343 A1 | 11/2005 |
| WO | WO 2006010574 A1 | 2/2006 |
| WO | WO 2006019715 A1 | 2/2006 |
| WO | 06/024471 A1 | 3/2006 |
| WO | WO 2006024471 A1 | 3/2006 |
| WO | WO 2006/96434 A2 | 9/2006 |
| WO | WO 2006096435 A1 | 9/2006 |
| WO | WO 2006125041 A1 | 11/2006 |
| WO | WO 2007014929 A1 | 2/2007 |
| WO | WO 2007/23325 A2 | 3/2007 |
| WO | WO 2007048803 A1 | 5/2007 |
| WO | WO 2007090091 A2 | 8/2007 |
| WO | WO 2008/06839 A2 | 1/2008 |
| WO | WO 2008006838 A1 | 1/2008 |
| WO | WO 2008/22932 A2 | 2/2008 |
| WO | WO 2008019996 A2 | 2/2008 |
| WO | WO 2008116890 A2 | 10/2008 |

OTHER PUBLICATIONS

Advisory Action dated Mar. 2, 2011; U.S. Appl. No. 11/745,515, filed May 8, 2007, 3 pgs.
Advisory Action dated Mar. 2, 2011; U.S. Appl. No. 11/554,855, filed Oct. 31, 2006, 3 pgs.
RCE dated Mar. 7, 2011; U.S. Appl. No. 11/837,957, filed Aug. 13, 2007, 2 pgs.
Response to Final Office Action dated Mar. 7, 2011; U.S. Appl. No. 11/837,957, filed Aug. 13, 2007, 9 pgs.
Response to Office Action dated Mar. 14, 2011; U.S. Appl. No. 11/097,939, filed Apr. 4, 2005, 20 pgs.
Interview Summary dated Mar. 15, 2011; U.S. Appl. No. 11/097,939, filed Apr. 4, 2005, 4 pgs.
Interview Summary dated Apr. 6, 2011; U.S. Appl. No. 11/997,567, filed Mar. 21, 2008, 3 pgs.
Response/Amendment dated Apr. 12, 2011; U.S. Appl. No. 11/997,567, filed Mar. 21, 2008, 9 pgs.
Final Office Action dated Apr. 19, 2011, U.S. Appl. No. 11/278,551, filed Apr. 4, 2006, 9 pgs.
Response to Office Action dated May 2, 2011; U.S. Appl. No. 12/390,665, filed Feb. 23, 2009, 11 pgs.
Office Action dated May 27, 2011; U.S. Appl. No. 12/170,884, filed Jul. 10, 2008, 6 pgs.
Office Action dated May 31, 2011; U.S. Appl. No. 11/097,939, filed Apr. 4, 2005, 15 pgs.
Final Office Action dated Jun. 16, 2011; U.S. Appl. No. 11/956,949, filed Dec. 14, 2007, 7 pgs.
Final Office Action dated Jun. 23, 2011; U.S. Appl. No. 11/997,567, filed Mar. 21, 2008, 7 pgs.
Restriction Requirement dated Jun. 29, 2011, U.S. Appl. No. 12/306,945, filed Feb. 9, 2009, 7 pgs.
U.S. Appl. No. 12/987,388, filed Jan. 10, 2011, Mendla et al.
Anderson et al., Guidelines for choice of selective serotonin reuptake inhibitor in depressive illness, Adv. Psychia. Treatment, 2001, 7:170-180.

Anonymous, Gel significantly increases sexual-activity in surgically menopausal women, Online, Nov. 1, 2004, XP002455243, Retrieved from the Internet: URL:http/www.news-medical.net/print_article.asp?id=5960>[retrieved on Oct. 17, 2007] 8 pgs.
Anonymous: "Hormone Patch May Provide Some Increase in Sexual Desire in Menopausal Women" Jul. 25, 2005; URL:http://pubs.ama-assn.org/media/2005a/0725.dtl , 2pgs.
Freeman et al., Differential Response to Antidepressants in Women With Premenstrual Syndrome/Premenstrual Dysphoric Disorder, Arch Gen Phych, 1999, 56:932-939.
Yekimov, Sex toys and devices in sexual dysfunction therapy, www.mosmedclinic.ru/conf_library/2002/2/130/, 2002, 6 pgs.
Richelson, Pharmacology of Antidepressants, Mayo Clin Proc., 2001, 76:511-527.
Werneke et al., Antidepressants and sexual dysfuntion, Acta Psychia. Scand, 2005, 114:384-397.
Response to Final Office Action dated Jul. 20, 2010; U.S. Appl. No. 11/740,959, filed Apr. 27, 2007, 14 pgs.
Response to Office Action dated Jul. 26, 2010; U.S. Appl. No. 11/837,957, filed Aug. 13, 2007, 11 pgs.
Restriction Requirement dated Oct. 4, 2005; U.S. Appl. No. 10/444,892, filed May 22, 2003, 7 pgs.
Response to Restriction Requirement dated Dec. 1, 2005; U.S. Appl. No. 10/444,892, filed May 22, 2003, 2 pgs.
RCE dated Jul. 20, 2010; U.S. Appl. No. 11/740,959, filed Apr. 27, 2007, 3pgs.
Response to Final Office Action dated Aug. 17, 2010; U.S. Appl. No. 11/097,939, filed Apr. 4, 2005, 22 pgs.
RCE dated Aug. 17, 2010; U.S. Appl. No. 11/097,939, filed Apr. 4, 2005, 3 pgs.
RCE dated Sep. 27, 2010, U.S. Appl. No. 11/837,959, filed Aug. 13, 2007, 2 pg.
Response to Final Office Action dated Sep. 27, 2010, U.S. Appl. No. 11/837,959, filed Aug. 13, 2007, 20 pgs.
Response to Final Office Action dated Sep. 27, 2010 U.S. Appl. No. 11/278,551, filed Apr. 4, 2006, 8 pgs.
Interview Summary dated Jul. 19, 2010; U.S. Appl. No. 11/740,959, filed Apr. 27, 2007, 3pgs.
Final Office Action dated Aug. 20, 2010 U.S. Appl. No. 11/745,515, filed May 8, 2007, 7 pgs.
Final Office Action dated Aug. 30, 2010 U.S. Appl. No. 11/554,855, filed Oct. 31, 2006, 10 pgs.
Notice of Missing Requirements dated Aug. 24, 2010 U.S. Appl. No. 12/675,231, filed Feb. 25, 2010, 2 pgs.
Interview Summary dated Aug. 25, 2010 U.S. Appl. No. 11/278,551, filed Apr. 4, 2006, 3 pgs.
Final Office Action dated Sep. 13, 2010, U.S. Appl. No. 11/837,962, filed Aug. 13, 2007, 20 pgs.
Office Action dated Sep. 14, 2010; U.S. Appl. No. 11/097,939, filed Apr. 4, 2005, 18 pgs.
Interview Summary dated Sep. 15, 2010, U.S. Appl. No. 11/837,959, filed Aug. 13, 2007, 4 pg.
Notice of Allowance dated Sep. 20, 2010 U.S. Appl. No. 12/091,848, filed Apr. 28, 2008, 7 pgs.
Final Office Action dated Oct. 6, 2010; U.S. Appl. No. 11/837,957, filed Aug. 13, 2007, 10 pgs.
Response to Final Office Action dated Oct. 12, 2010; U.S. Appl. No. 11/960,957, filed Dec. 20, 2007, 16 pgs.
Interview Summary dated Oct. 19, 2010; U.S. Appl. No. 11/997,567, filed Mar. 21, 2008, 3 pgs.
Response to Final Office Action dated Oct. 21, 2010; U.S. Appl. No. 11/997,567, filed Mar. 21, 2008, 8 pgs.
RCE dated Oct. 21, 2010; U.S. Appl. No. 11/997,567, filed Mar. 21, 2008, 2 pgs.
Interview Substance dated Oct. 21, 2010; U.S. Appl. No. 11/997,567, filed Mar. 21, 2008, 1 pg.
Office Action dated Oct. 26, 2010, U.S. Appl. No. 11/278,551, filed Apr. 4, 2006, 10 pgs.
Office Action dated Nov. 5, 2010; U.S. Appl. No. 11/956,949, filed Dec. 14, 2007, 10 pgs.
Advisory Action dated Nov. 8, 2010; U.S. Appl. No. 11/960,957, filed Dec. 20, 2007, 3 pgs.

(56) References Cited

OTHER PUBLICATIONS

Acknowledgment of Priority Document dated Nov. 4, 2010; U.S. Appl. No. 12/091,848, filed Apr. 28, 2008, 1 pg.
Office Action dated Nov. 12, 2010; U.S. Appl. No. 11/997,567, filed Mar. 21, 2008, 7 pgs.
Notice of Allowance dated Nov. 15, 2010; U.S. Appl. No. 12/091,848, filed Apr. 28, 2008, 4 pgs.
RCE dated Dec. 20, 2010; U.S. Appl. No. 12/091,848, filed Apr. 28, 2008, 3 pgs.
Office Action dated Dec. 30, 2010; U.S. Appl. No. 12/390,665, filed Feb. 23, 2009, 9 pgs.
Response to Final Office Action dated Jan. 20, 2011; U.S. Appl. No. 11/745,515, filed May 8, 2007, 7 pgs.
Response to Final Office Action dated Jan. 20, 2011; U.S. Appl. No. 11/554,855, filed Oct. 31, 2006, 9 pgs.
Response to Office Action dated Jan. 28, 2011, U.S. Appl. No. 11/278,551, filed Apr. 4, 2006, 7 pgs.
Response to Final Office Action dated Feb. 7, 2011; U.S. Appl. No. 11/837,957, filed Aug. 13, 2007, 9 pgs.
RCE dated Feb. 15, 2011; U.S. Appl. No. 11/837,962, filed Aug. 13, 2007, 2 pgs.
Response to Final Office Action dated Feb. 15, 2011; U.S. Appl. No. 11/837,962, filed Aug. 13, 2007, 15 pgs.
Notice of Allowance dated Feb. 16, 2011; U.S. Appl. No. 12/091,848, filed Apr. 28, 2008, 8 pgs.
Advisory Action dated Feb. 17, 2011; U.S. Appl. No. 11/837,957, filed Aug. 13, 2007, 3 pgs.
Notice of Appeal dated Feb. 22, 2011; U.S. Appl. No. 11/745,515, filed May 8, 2007, 1 pgs.
Notice of Appeal dated Feb. 22, 2011; U.S. Appl. No. 11/554,855, filed Oct. 31, 2006, 1 pgs.
FDA (U.S. Food and Drug Administration); Reproductive Health Drugs Advisory Committee Meeting Announcement; URL: http://www.fda.gov/AdvisoryCommittees /Calendar/ucm210886.htm; Jun. 18, 2010; 1 pg.
Background Document for Meeting of Advisory Committee for Reproductive Health Drugs (Jun. 8, 2010); NDA 22-526 Flibanserin; Boehringer Ingelheim; May 20, 2010; 80 pgs.
Briefing Document; Flibanserin (BIMT 17 BS); Boehringer Ingelheim; May 14, 2010; 248 pgs.
FDA (U.S. Food and Drug Administration); Reproductive Health Drugs Advisory Committee Meeting; Draft Agenda; Jun. 18, 2010; 1 pg.
FDA (U.S. Food and Drug Administration); Reproductive Health Drugs Advisory Committee Meeting; Draft Questions to the Committee; Jun. 18, 2010; 1 pg.
FDA (U.S. Food and Drug Administration); Reproductive Health Drugs Advisory Committee Meeting; Draft Meeting Roster; Jun. 18, 2010; 2 pgs.
Advisory Committee for Reproductive Health Drugs—2010 Members; Jun. 2010; 2 pgs.
FDA (U.S. Food and Drug Administration); Reproductive Health Drugs Advisory Committee Meeting; Agenda; Jun. 18, 2010; 2 pgs.
FDA (U.S. Food and Drug Administration); Reproductive Health Drugs Advisory Committee Meeting; Questions to the Committee; Jun. 18, 2010; 1 pgs.
FDA (U.S. Food and Drug Administration); Reproductive Health Drugs Advisory Committee Meeting; Meeting Roster; Jun. 18, 2010; 2 pgs.
(Slides) Division of Reproductive and Urologic Drug Products Advisory Committee Meeting; Flibanserin (NDA-22526); Boehringer Ingelheim; Jun. 18, 2010; 110 pgs.
Press Release May 19, 2010; women with hypoactive sexual desire disorder (HSDD) report that fibanserin increased their sexual desire and reduced associated distress; http://www.boehringer-ingelheim.com/news/news releases/press releases/2010/19 May 2010; 4 pgs.
Press Release Jun. 17, 2010; Key Facts on HSDD and Flibanserin; http://us.boerhinger-ingelheim.com/news events/press releases/ press release archive/2010; 2 pgs.

Press Release Jun. 18, 2010; Boehringer Ingelheim comments on Jun. 18th FDA Advisory Committee Meeting; http://us.boehringer-ingelheim.com/news events/press releases; press release archive/ 2010; 2 pgs.
FDA (U.S. Food and Drug Administration); Transcript of Advisory Committee for Reproductive Health Drugs; Jun. 18, 2010; 293 pgs.
U.S. Appl. No. 12/280,804, filed Aug. 27, 2008, Ceci.
U.S. Appl. No. 12/306,946, filed Dec. 29, 2008, Becker.
U.S. Appl. No. 12/306,945, filed Dec. 29, 2008, Pyke.
U.S. Appl. No. 12/306,878, filed Dec. 29, 2008, Castrol et al.
Alexander et al., J. of Am. Acad. of Nurse Practitioners, 2007, 19:152-163.
Guilleminault et al., Atypical Sexual Behavior During Sleep, Phychosomatic Med., 2002, 64:328-336.
Basson et al., Sexual psychophysiology and effects of sildenafil citrate in oestrogenised women with acquired genital arousal disorder and impaired orgasm: a randomised controlled trial, BJOG: an International Journal of Obstetrics and Gyn., Nov. 2003, 110:1014-1024.
Basson et al., Efficacy and Safety of Sildenafil Citrate in Women with Sexual Dysfunction Associated with Female Sexual Arousal Disorder, J Women's Health & Gender-Based Medicine, Nov. 4, 2002 11:367-77.
Black et al., Inappropriate sexual behaviors in dementia, J of Geriatric Psychiatry & Neurology, Sep. 2005, 18(3):155-162.
Clayton, Epidemiology and Neurobiology of Femal Sexual Dysfunction, J Sex Med., Nov. 4, 2007, Suppl 4:260-8.
Clayton et al., Burden of phase-specific sexual dysfunction with SSRIs, J Affect Disord., Mar. 2006, 91(1):27-32.
Clayton et al., Prevalence of Sexual Dysfunction Among Newer Antidepressants, J. Clin. Psychiatry, 2002, 63(4):357-366.
CMU Pharmaceutical polymorphism, http://www.andrew.cmu.edu/user/suter/polymorph.html, internet p. 1-3 (2002): obtained Feb. 11, 2009.
Sexual Dysfunction and Hypotestosteronemia in Patients With Obstructive Sleep Apnea Syndrome and Its Effects With CPAP Therapy, http:..clinicaltrials.gov/ct2/show/NCT00832065, obtained Apr. 1, 2009, 4pgs.
Doelker et al., Crystalline modifications and polymorphism changes during drug manufacturing, Annales Pharmaceutiques Francaises, 2002, 60(3):161-169.
Doelker et al., Physicochemical behavior or active substances. Consequences for the feasibility and stability of pharmaceutical forms, S.T.P. Pharma Pratiques, 1999, 9(5):399-409.
Engleson, Concise Encyclopedia Chemistry, 1993, pp. 872-873.
Giraldi et al., Physiology of Female Sexual Function: Animal Models, J Sex Med, 2004, 1(3):237-253.
Girgis et al., A double-blind trial of clomipramine in premature ejaculation, Andrologia, Jul.-Aug. 1982, 14(4):364-8.
Goldfischer et al., Selected 2008 Abstracts from the International Society for the Study of Women's Sexual Health, J. Sex. Med., 2008, 5(suppl. 3):159-160.
Goodman, An assessment of clomipramine (Anafranil) in the treatment of premature ejaculation, J Int Med Res., 1980; 8(Suppl 3):53-9.
Haensel et al., Fluoxetine and premature ejaculation: a double-blind, crossover, placebo-controlled study, J Clin Psychopharmacology, 1998, 18:72-77.
Haensel et al., Clomipramine and sexual function in men with premature ejaculation and controls, J Urology, Oct. 1996, 156(B193):1310-1315.
Jain et al., Polymorphism in Pharmacy, Indian Drugs, 1986, 23(6):315-329.
Kandeel et al., Male Sexual Function and its Disorders: Physiology, Pathophysiology, Clinical investigation, and Treatment, Endocrine Reviews, 2001, 22(3):342-388 at 370.
Kennedy et al., Antidepressant-Induced Sexual Dysfunction During Treatment with Moclobemide, Paroxetine, Sertraline, and Venlafaxine, J Clin Psychiatry, 2000; 61:276-81.
Kennedy et al., Sexual dysfunction before antidepressant therapy in major depression, J. Affective Disorders, 1999, 56:201-208.
Konarski et al., Effects of Acute Flibanserin on FDG-PET Brain Glucose Metabolism in Men with Major Depressive Disorder, Aug.

(56) References Cited

OTHER PUBLICATIONS

2008 Barcelona meeting of the European College of Nueropsychopharmacology, 3 pgs. (poster-abstract).
McKenna, Neural Circuitry Involved in Sexual Function, J Spinal Cord Med., 2001, 24:148-154.
McMahon et al., Efficacy of type-5 phosphodiesterase inhibitors in the drug treatment of premature ejaculation: a systematic review, BJU Int., 2006, 98:259-72.
Montejo-Gonzales et al., SSRI-induced sexual dysfunction: fluoxetine, paroxetine, sertraline, and fluvoxamine in a prospective, multicenter, and descriptive clinical study of 344 patients, J Sex Marital, 1997 Fall; 23(3):176-94.
Muzaffar et al., J. Pharmacy, 1979, 1(1):59-66.
Nurnberg et al., Sildenafil for Sexual Dysfunction in Women Taking Antidepressants, Am J Psychiatry, October—Letters to the Editor, 1999, 156(10):1664.
Nurnberg et al., Sildenafil Treatment of Women with Antidepressant-Associated Sexual Dysfunction, JAMA, Jul. 2008, 300(4):395-404.
Pfaus et al., What can animal models tell us about human sexual response?, Annu Rev Sex Res, 2003, 14:1-63.
Porter, Remingtons, 1990, Chpt 90, pp. 1666-1675.
Pryor et al., Efficacy and tolerability of dapoxetine in treatment of premature ejaculation: an integrated analysis of two double-blind, randomized controlled trials, Lancet, 2006, 368(9539):929-37.
Pyke et al., Flibanserin: A Novel Centrally Acting Agent that is not an Effective Antidepressant but has Potential to Treat Decreased Sexual Desire in Women, APA, May 2008, 1 pg. (accepted poster).
Pyke et al., Flibanserin: A Novel Centrally Acting Agent that is not an Effective Antidepressant but has Potential to Treat Decreased Sexual Desire in Women, APA, May 2008, 1 pg. (accepted abstract).
Rapkin, General Gynecology, 2007, 196:97-106.
Rendell et al., Sildenafil for Treatment of Erectile Dysfunction in Men with Diabetes, JAMA, 1999, 281:421-426.
Rosen et al., Effects of SSRIs on sexual function: a critical review, J Clin Psychopharmacol., Feb. 1999 19(1):67-85.
Rosen et al., PDE-5 inhibition and sexual response: Pharmacological mechanisms and clinical outcomes, Annual Review of Sex Res, 2002, pp. 36-88.
Rosen, Sexual pharmacology in the 21st century, J Gend Specif Med., Jul.-Aug. 2000, 3(5):45-52.
Rowland, Neurobiology of Sexual Response in Men and Women, 1:CNS Spectr., Aug. 2006, 11(8 Suppl 9):6-12.
Rubenstein, Pharmaceutics: The Science of Dosage Form Design, ed. Aulton, 1988, pp. 304-321.
Martin, Sexsomnia, http://lakesidepress.com/pulmonary/ Sleep/sexsomnia.html, obtianed Apr. 1, 2009, 5pgs.
Stearns et al., J. of Clin. Oncology, 2002, 20(6):1436-1438.
Stedman's Medical Dictionary definition "Prevention," 2000, 28th Ed., 3 pgs., Lippincott Williams & Wilkins.
Stoleru et al., Brain processing of visual sexual stimuli in men with hypoactive sexual desire disorder, Psychiatry Res.: Neuroimaging, 2003, 124(2):67-86.
Clayton et al., Validation of the Decreased Sexual Desire Screener (DSDS): a Brief Diagnostic Instrument for Generalized, Acquired Hypoactive Sexual Desire Disorder in Women, International Society for the Study of Womens Sexual Health (ISSWSH) annual meeting, 2007, 2 pgs. (poster and abstract).
Wunderlich et al., Using e-Diaries to Measure Sexual Desire in Women with Hypoactive Sexual Desire Disorder, International Society for the Study of Womens Sexual Health (ISSWSH) annual meeting, 2007, 11 pgs. (Oral Presentation).
Clayton et al., Validation of the Sexual Interest and Desire Inventory-Female (SIDI-F) in North American Women, International Society for the Study of Womens Sexual Health (ISSWSH) annual meeting, 2007, 3 pgs. (poster and abstract).
Clayton et al., Validity of Sexual Distress Scales vs Electronic Diary in Women with Decreased Sexual Desire , American College of Obstetrics and Gynecologists (ACOG) annual meeting, 2007, 1 pg. (abstract only).
Clayton et al., Validating the Sexual Interest and Desire Inventory (SIDI-F) in North American Women , American College of Obstetrics and Gynecologists (ACOG) annual meeting, 2007, 1 pg. (abstract only).
Clayton et al., Validation of the Sexual Interest and Desire Inventory-Female (SIDI-F) in North American Women, American Psychiatric Association (APA) annual meeting, 2007, 2 pgs. (poster and abstract).
Tignol et al., Using e-Diaries to Measure Sexual Desire in Women with Hypoactive Sexual Desire Disorder, European Society for Sexual Medicine (ESSM) annual meeting, 2007, 9 pgs. (oral presentation).
Clayton, Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 10 pgs. (oral presentation).
Clayton et al., Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 1 pgs. (abstract).
Clayton et al., Baseline characteristics of patients enrolled in three Phase III North American trials of flibanserin in premenopausal women with Hypoactive Sexual Desire Disorder, International Society for the Study of Womens Sexual Health (ISSWSH) annual meeting 2009, poster, 2 pgs. (poster and abstract).
Clayton et al., Validation of the Decreased Sexual Desire Screener (DSDS): A Brief Diagnostic Instrument for Generalized Acquired Female Hypoactive Sexual Desire Disorder (HSDD); J. Sex Med., 2009, pp. 1-9. (epub ahead of print).
Dean, Decreased Sexual Desire Screener © (DSDS ©) for Diagnosis of Hypoactive Sexual Desire Disorder in Women, WONCA Europe conference, 2008, 8 pgs. (oral presentation).
Dean et al., Decreased Sexual Desire Screener © (DSDS ©) for Diagnosis of Hypoactive Sexual Desire Disorder in Women, WONCA Europe conference, 2008, 1 pg. (abstract).
Derogatis et al., Validation of Sexual Distress Scales and Electronic Diary in Women with Hypoactive Sexual Desire Disorder, International Society for the Study of Womens Sexual Health (ISSWSH) annual meeting, 2007, 3 pgs. (poster and abstract).
Derogatis et al., Validation of Sexual Distress Scales and Electronic Diary in Women with Hypoactive Sexual Desire Disorder. American Psychiatric Association (APA) annual meeting, 2007, 2 pgs. (poster and abstract).
Derogatis et al., Content Validity of the Female Sexual Distress Scale-Revised (FSDS-R) in Women with Hypoactive Sexual Desire Disorder (HSDD), Joint Congress of the European and International Societies of Sexual Medicine (ESSM/ISSM) 2008, 5 pgs. (poster, oral presentation and abstract).
Derogatis et al., Validation of the Female Sexual Distress Scale Revised (FSDS-R) for assessing distress in women with Hypoactive Sexual Desire Disorder (HSDD), J Sex Med., 2008, 5:357-364.
Dennerstein et al., Differentiating Four Cognitive-Behavioral Types of Women with Low Sexual Desire, International Society for the Study of Womens Sexual Health (ISSWSH) annual meeting, 2007, 9 pgs. (Oral Presentation).
Dennerstein et al., Differentiating Four Cognitive-Behavioral Types of Women with Decreased Sexual Desire, International Society for the Study of Womens Sexual Health (ISSWSH) annual meeting, 2007, 2 pgs. (abstract).
Dennerstein et al., Differentiating Four Cognitive-Behavioral Types of Women with Decreased Sexual Desire, American Psychiatric Association (APA) annual meeting, 2007, 3 pgs. (poster and abstract).
Dennerstein et al., Differentiating Four Cognitive-Behavioral Types of Women with Decreased Sexual Desire, European Society for Sexual Medicine (ESSM) annual meeting, 2007, 3 pgs. (poster and abstract).
Dennerstein, Differentiating Four Cognitive-Behavioral Types of Women with Low Sexual Desire, European Society for Sexual Medicine (ESSM) annual meeting, 2007, 10 pgs. (oral presentation).

(56) References Cited

OTHER PUBLICATIONS

Dennerstein et al., Attitudes Towards Partner Interactions of Women With Characteristics of HSDD: Preliminary Results of a Multinational Study of 1,402 Women. International Society for the Study of Womens Sexual Health (ISSWSH) annual meeting, 2008, 12 pgs. (oral presentation and abstract).

Goldfischer et al., Validation of the Decreased Sexual Desire Screener (DSDS): a Brief Diagnostic Instrument for Generalized, Acquired Hypoactive Sexual Desire Disorder in Women, American Psychiatric Association (APA) annual meeting, 2007, 2 pgs. (poster and abstract).

Pyke et al., The Rose Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (poster).

Goldfischer et al., Efficacy of Continued Flibanserin Treatment on Sexual Desire and Satisfying Sexual Events in Premenopausal Women With HSDD: Results From the ROSE Study, International Society for the Study of Womens Sexual Health (ISSWSH) annual meeting, 2008, 1 pgs. (abstract).

Goldfischer et al., Efficacy of Continued Flibanserin Treatment on Distress Associated with Sexual Dysfunction in Premenopausal Women With HSDD: Results From the ROSE Study, International Society for the Study of Womens Sexual Health (ISSWSH) annual meeting, 2008, 2 pgs. (poster and abstract).

Goldfischer et al., Efficacy of Continued Flibanserin Treatment on Sexual Functioning in Premenopausal Women With HSDD: Results From the ROSE Study, International Society for the Study of Womens Sexual Health (ISSWSH) annual meeting, 2008, oral presentation, 1 pg. (abstract only).

Goldfischer et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 1 pg. (abstract only).

Goldfischer et al., The ROSE Study: Placebo-controlled Randomized Withdrawal Trial of Flibanserin for Hypoactive Sexual Desire Disorder in Premenopausal Women. European Federation of Sexology (EFS), 2008, 7 pgs. (oral presentation and abstract).

Goldfischer et al., Decreased Sexual Desire Screener (DSDS) for Diagnosis of Hypoactive Sexual Desire Disorder in Women, American College of Obstetrics and Gynecologists (ACOG) annual meeting, 2008, 2 pgs. (poster and abstract).

Goldfischer et al., Efficacy of Continued Flibanserin Treatment in Premenopausal Women with Hypoactive Sexual Desire Disorder: Results from the ROSE Study, International Academy of Sex Research (IASR) annual meeting, 2008, 3 pgs. (poster and abstract).

Goldfischer et al., Safety and Tolerability of Flibanserin in Premenopausal Women with Hypoactive Sexual Desire Disorder: Results from the ROSE Study, International Academy of Sex Research (IASR) annual meeting, 2008, 3 pgs. (poster and abstract).

Goldfischer et al., Efficacy and Safety of Flibanserin in Premenopausal Women with Hypoactive Sexual Desire Disorder: Results from the Randomized Withdrawal ROSE Study, Institute on Psychiatric Services (IPS) annual meeting, 2008, 2 pgs. (poster and abstract).

Goldfischer et al., Decreased Sexual Desire Screener (DSDS) for Diagnosis of Hypoactive Sexual Desire Disorder in Women, Sexual Medicine Society of North America (SMSNA) annual meeting, 2008, 3 pgs. (poster and abstract).

Goldfischer et al., Efficacy and Safety of Flibanserin in Premenopausal Women with Hypoactive Sexual Desire Disorder: Results From the Randomized Withdrawal ROSE Study, Sexual Medicine Society of North America (SMSNA) annual meeting, 2008, 3 pgs. (poster and abstract).

Goldfischer, Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 10 pgs. (oral presentation).

Goldfischer et al., Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (abstract).

Goldfischer et al., Safety and Tolerability of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (poster and abstract).

Goldstein et al., Differences in Patient-Physician Communication Regarding Hypoactive Sexual Desire Disorder (HSDD), Sexual Medicine Society of North America (SMSNA) annual meeting, 2007, 3 pgs. (poster and abstract).

Goldstein et al., Emotions Related to Distress in Patients with Hypoactive Sexual Desire Disorder: Results of Patient and Physician Interviews, Sexual Medicine Society of North America (SMSNA) annual meeting, 2007, 3 pgs. (poster and abstract).

Jolly et al., Design of Phase III Pivotal Trials of Flibanserin in Female Hypoactive Sexual Desire Disorder (HSDD), European Federation of Sexology (EFS), 2008, 2 pgs. (poster and abstract).

Nappi et al., Validation of the Sexual Interest and Desire Inventory-Female (SIDI-F) in European Women, European Federation of Sexology (EFS), 2008, 2 pgs. (poster and abstract).

Nappi, Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 8 pgs. (oral presentation).

Nappi et al., Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 1 pg. (abstract).

Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 8 pgs. (oral presentation).

Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 1 pg. (abstract).

Pyke et al., Using e-Diaries to Measure Sexual Desire in Women with Hypoactive Sexual Desire Disorder, American Psychiatric Association (APA) annual meeting, 2007, 2 pgs. (poster and abstract).

Pyke et al., The ROSE Study: Placebo-Controlled Randomized Withdrawal Trial of Flibanserin for Hypoactive Sexual Desire Disorder in Premenopausal Women (Study Design Only), Institute on Psychiatric Services (IPS) annual meeting, 2007, 2 pgs. (poster and abstract).

Pyke et al., Safety and Tolerability of Flibanserin in Premenopausal Women With Hypoactive Sexual Desire Disorder (HSDD): Results From the ROSE Study, American Psychiatric Association (APA) annual meeting, 2008, 2 pgs. (poster and abstract).

Pyke et al., Flibanserin: a Novel Centrally Acting Agent That is not an Effective Antidepressant but has Potential to Treat Decreased Sexual Desire in Women, American Psychiatric Association (APA) annual meeting, 2008, 2 pgs. (poster and abstract).

Rosen et al., The Predictors of Sexual Distress in Women With Low Sexual Desire, International Society for the Study of Womens Sexual Health (ISSWSH) annual meeting, 2009, oral presentation, 15 pgs. (oral presentation and abstract).

Shifren et al., Sexual Problems and Distress in United States Women: Prevalence and Correlates, Obstet. Gynecology, Nov. 2008, 112(5):970-978.

Shifren et al., Treatment-seeking Behavior of U.S. Women with Hypoactive Sexual Desire Disorder (HSDD), American College of Obstetrics and Gynecologists (ACOG) annual meeting, 2008, 2 pgs. (poster and abstract).

(56) References Cited

OTHER PUBLICATIONS

Pyke et al., Validation of the Sexual Interest and Desire Inventory-Female (SIDI-F) in European Women, International Society for the Study of Womens Sexual Health (ISSWSH) annual meeting, 2007, 20 pgs. (oral presentation).
Nappi et al., Validation of the Sexual Interest and Desire Inventory-Female (SIDI-F) in European Women, European Society for Sexual Medicine (ESSM) annual meeting, 2007, 19 pgs. (oral presentation).
Sand et al., The Female Sexual Function Index (FSFI): A Potential "Gold Standard" Measure for Assessing Therapeutically-Induced Change in Female Sexual Function, ASRM, 2009, Oct. 17-21, 2009, Atlanta, Georgia, 2 pgs. (poster and abstract).
Smith et al., Pharmacokinetics of Flibanserin in Premenopausal Women With Hypoactive Sexual Desire Disorder Including Effects on the Female Sexual Function Index, ESSM, 2009, Nov. 2009, 2 pgs., Lyon. (poster and abstract).
Clayton et al., Efficacy of Flibanserin As a Potential Treatment for Hypoactive Sexual Desire Disorder in North American Premenopausal Women: Results From The Dahlia Trial, ESSM, 2009, Nov. 2009, 2 pgs., Lyon. (poster and abstract).
Thorp et al., Efficacy of Flibanserin As a Potential Treatment for Hypoactive Sexual Desire Disorder in North American Premenopausal Women: Results From the Daisy Trial, ESSM, 2009, Nov. 2009, 3 pgs., Lyon. (poster and abstract).
Jolly et al., Design of Randomized Controlled Trials of Flibanserin in Premenopausal Women With Hypoactive Sexual Desire Disorder, ESSM 2009, Nov. 2009, 3 pgs., Lyon. (poster and abstract).
Revicki et al., Content Validity of the Female Sexual Function Index in Pre- and Postmenopausal Women With Hypoactive Sexual Desire Disorder, ESSM 2009, Nov. 2009, 2 pgs., Lyon. (poster and abstract).
Aubert et al., Comparison of Flibanserin With the 5-Htla Agonist (+)-8-Oh-Dpat in Affecting Interactions Between Male-Female Marmoset Pairs, ESSM 2009, Nov. 2009, 2 pgs., Lyon (poster and abstract).
Rosen et al., Criterion Validity of the Sexual Desire Domain of the Female Sexual Function Index (Fsfi): Identifying a Diagnostic Cut-Point for Differentiating Women With and Without Hsdd, ESSM 2009, Nov. 2009, 3 pgs., Lyon. (poster and abstract).
Rosen et al., Validation of the FSFI Sexual Desire Domain Diagnostic Cut-Point in Predicting Hsdd in Women: Independent Replication and Confirmation, ESSM 2009, Nov. 2009, 2 pgs., Lyon. (poster and abstract).
Nappi, Efficacy of Flibanserin As a Potential Treatment for Hypoactive Sexual Desire Disorder in European Premenopausal Women: Results From the Orchid Trial; ESSM 2009, Nov. 2009, 12 pgs., Lyon. (oral presentation).
Nappi et al., Efficacy of Flibanserin As a Potential Treatment for Hypoactive Sexual Desire Disorder in European Premenopausal Women: Results From the Orchid Trial; ESSM 2009, Nov. 2009, 1 pg., Lyon. (abstract).
Holstege et al., Differences in Brain Activity in Premenopausal Women With Hypoactive Sexual Desire Disorder (Hsdd) Compared to Women Without Sexual Dysfunction, ESSM 2009, Nov. 2009, 2 pgs., Lyon. (abstract only).
Holstege et al., Brain activation and de-activation caused by erotic movies is lower in HSDD—than in non-HSDD volunteers, ESSM 2009, 8 pgs. (oral presentation).
Jolly, Efficacy of Flibanserin 100 Mg Qhs As a Potential Treatment for Hypoactive Sexual Desire Disorder in Premenopausal Women, ESSM 2009, Nov. 2009, 12 pgs., Lyon. (oral presentation).
Jolly et al., Efficacy of Flibanserin 100 Mg Qhs As a Potential Treatment for Hypoactive Sexual Desire Disorder in Premenopausal Women, ESSM 2009, Nov. 2009, 1 pgs., Lyon. (abstract).
Jolly et al., Efficacy of Flibanserin 100 Mg Qhs As a Potential Treatment for Hypoactive Sexual Desire Disorder in North American Premenopausal Women, ESSM 2009, Nov. 2009, 2 pgs., Lyon. (poster and abstract).
Clayton, Safety and Tolerability of Flibanserin in Premenopausal Women With Hypoactive Sexual Desire Disorder, ESSM 2009, Nov. 2009, 12 pgs., Lyon. (oral presentation).
Jolly et al., Safety and Tolerability of Flibanserin in Premenopausal Women With Hypoactive Sexual Desire Disorder, ESSM 2009, Nov. 2009, 1 pg., Lyon. (abstract).
Jolly et al., Efficacy of Flibanserin As a Potential Treatment for Hypoactive Sexual Desire Disorder in North American Premenopausal Women: Results From the Violet Trial, ESSM 2009, Nov. 2009, 3 pgs., Lyon. (poster and abstract).
Fuchs, Baseline Characteristics of Patients Enrolled in Three Phase III North American Trials of Flibanserin in Premenopausal Women With Hypoactive Sexual Desire Disorder, FIGO 2009, Oct. 2009, 10 pgs., Cape Town, South Africa. (oral presentation).
Goldfischer, Efficacy and Safety of Flibanserin in a Randomized Withdrawal Study of Premenopausal Women With Hypoactive Sexual Desire Disorder, FIGO2009, Oct. 2009, 12 pgs., Cape Town, South Africa. (oral presentation).
Goldfischer et al., Efficacy and Safety of Flibanserin in a Randomized Withdrawal Study of Premenopausal Women With Hypoactive Sexual Desire Disorder, FIGO2009, Oct. 2009, 1 pgs., Cape Town, South Africa. (abstract).
Revicki et al., Content Validity of the Female Sexual Function Index in Pre- and Postmenopausal Women With Hypoactive Sexual Desire Disorder, ICSM 2009, Jul. 2009, 2 pgs., Paris. (poster and abstract).
Revicki et al., Content Validity of the Female Sexual Function Index in Pre-Menopausal Women With Hypoactive Sexual Desire Disorder, ICSM 2009, Jul. 2009, 2 pgs., Paris. (poster and abstract).
Rosen et al., Criterion Validity of the Sexual Desire Domain of the Female Sexual Function Index (Fsfi): Identifying a Diagnostic Cut-Point for Differentiating Women With and Without Hsdd, ICSM 2009, Jul. 2009, 2 pgs., Paris. (poster and abstract).
Rosen et al., Validation of the Fsfi Sexual Desire Domain Diagnostic Cut-Point in Predicting Hsdd: Independent Replication and Confirmation, ICSM 2009, Jul. 2009, 2 pgs., Paris. (poster and abstract).
Sand et al., The Female Sexual Function Index (Fsfi): A Potential "Gold Standard" Measure for Assessing Sexual Function in Women, ICSM 2009, Jul. 2009, 2 pgs., Paris. (poster and abstract).
Jayne, Results From the Dahlia (511.70) Trial: A Prospective Study of Flibanserin for the Treatment of Hypoactive Sexual Desire Disorder in North American Premenopausal Women, SMSNA 2009, Nov. 2009, 3 pgs,, San Diego, USA (oral presentation).
Jayne et al., Results From the Dahlia (511.70) Trial: A Prospective Study of Flibanserin for the Treatment of Hypoactive Sexual Desire Disorder in North American Premenopausal Women, SMSNA 2009, Nov. 2009, 2 pgs., San Diego, USA (abstract and poster).
Sand et al., Efficacy of Flibanserin in North American Premenopausal Women With Hypoactive Sexual Desire Disorder: Results From the Daisy Trial, SMSNA 2009, Nov. 2009, 2 pgs., San Diego, USA. (poster and abstract).
Sand, Efficacy of Flibanserin in North American Premenopausal Women With Hypoactive Sexual Desire Disorder: Results From the Daisy Trial, SMSNA 2009, Nov. 2009, 2 pgs., San Diego, USA. (oral presentation).
Sand et al., The Female Sexual Function Index (Fsfi) Is a Potential "Gold Standard" Measure for Assessing Sexual Function in Pre- and Post-Menopausal Women: a Systematic Review, SMSNA 2009, Nov. 2009, 2 pgs., San Diego, USA. (poster and abstract).
Sand et al., Efficacy of Flibanserin 100 Mg Qhs As a Potential Treatment for Hypoactive Sexual Desire Disorder in North American Premenopausal Women, SMSNA 2009, Nov. 2009, 2 pgs., San Diego, USA. (poster and abstract).
Sand, Efficacy of Flibanserin 100 Mg Qhs As a Potential Treatment for Hypoactive Sexual Desire Disorder in North American Premenopausal Women, SMSNA 2009, Nov. 2009, 2 pgs., San Diego, USA. (oral presentation).
Holstege et al., Differences in Brain Activity in Premenopausal Women With Hypoactive Sexual Desire Disorder (Hsdd) Compared to Women Without Sexual Dysfunction, SMSNA 2009, Nov. 2009, 2 pgs., San Diego, USA (abstract only).
Holstege et al., Brain activation and de-activation caused by erotic movies is lower in HSDD—than in non-HSDD volunteers, SMSNA, 2009, 4 pgs (poster & oral presentation).

(56) References Cited

OTHER PUBLICATIONS

Sand et al., Pooled Clinical Trail Analysis of Flibanserin Safety and Tolerability in Premenopausal Women with Hypoactive Sexual Desire Disorder, SMSNA, 2009, 2 pgs. (poster and abstract).
Sand, Pooled Clinical Trail Analysis of Flibanserin Safety and Tolerability in Premenopausal Women with Hypoactive Sexual Desire Disorder, SMSNA, 2009, 2 pgs. (oral presentation).
Sand et al., Effacacy of Flibanserin in North American Premenopausal Women with Hypoactive Sexual Desire Disorder: Results from the Violet Trial, SMSNA, 2009, 3 pgs. (poster and abstract).
Sand, Effacacy of Flibanserin in North American Premenopausal Women with Hypoactive Sexual Desire Disorder: Results from the Violet Trial, SMSNA, 2009, 2 pgs. (oral presentation).
Meston, The Female Sexual Function Index (FSFI) is a Potential "Gold Standard" Measure for Assessing Sexual Function in Pre- and post-menopausal Women: a Systematic Review, SMSNA, 2009, 3 pgs. (oral presentation).
Goldfischer, Efficacy and Safety of Flibanserin in a Randomized Withdrawal Study of Premenopausal Women With Hypoactive Sexual Desire Disorder, WAS, 2009, 12 pgs. (oral presentation).
Goldfischer et al., Efficacy and Safety of Flibanserin in a Randomized Withdrawal Study of Premenopausal Women With Hypoactive Sexual Desire Disorder, WAS, 2009, 1 pgs. (abst.).
Clayton et al., Baseline Characteristics of Patients Enrolled in Three Phase III North American Trials of Flibanserin in Premenopausaul Women with Hypoactive Sexual Desire Disorder, WAS, 2009, 2 pgs. (poster and abstract).
Clayton, Baseline Characteristics of Patients Enrolled in Three Phase III North American Trials of Flibanserin in Premenopausaul Women with Hypoactive Sexual Desire Disorder, WAS, 2009, 4 pgs. (oral presentation).
Derogatis et al., Content Validity of the Female Sexual Distress Scale-Revised in Women With Hypoactive Sexual Desire Disorder, WAS, 2009, 1 pg. (abstract only).
Dennerstein et al., Attitudes Toward and Frequency of Partner Interactions Among Women Reporting Decreased Sexual Desire, J. Sex Med., 2009, 6:1668-1673.
Goldstein et al., National Differences in Patient-Clinician Communication Regarding Hypoactive Sexual Desire Disorder, J. Sex Med., 2009, 6:1349-1357.
Johannes et al., Distressing Sexual Problems in United States Women Revisited: Prevalence After Accounting for Depression, J. Clin. Psych., 2009, 70(12):1698-1706.
Pfaus, Pathways of Sexual Desire, J. Sex Med., 2009, 6:1506-1533.
Rosen et al., Correlates of Sexually Related Personal Distress in Women with Low Sexual Desire, J. Sex Med., 2009, 6:1549-1560.
Lewis-D' Agostino et al., Validating the Sexual Interest and Desire Inventory (SIDI-F) in North American Women, American College of Obstetrics and Gynecologists (ACOG) annual meeting, 2007, 1 pg. (poster).
Shifren et al., Help-Seeking Behavior of Women with Self-Reported Distressing Sexual Problems, J. of Women's Health, 2009, 18(4):461-468.
Wunderlich et al., Validity of Sexual Distress Scales vs Electronic Diary in Women with Decreased Sexual Desire, American College of Obstetrics and Gynecologists (ACOG) annual meeting, 2007, 1 pg. (poster).
Clayton et al., Using e-Diaries to Measure Sexual Desire in Women with Hypoactive Sexual Desire Disorder, European Society for Sexual Medicine (ESSM) annual meeting, 2007, 2 pgs. (abstract).
Van Lunsen et al., Validation of the Sexual Interest and Desire Inventory-Female (SIDI-F) in European Women, European Society for Sexual Medicine (ESSM) annual meeting, 2007, 1 pg. (abstract).
Clayton et al., Using e-Diaries to Measure Sexual Desire in Women with Hypoactive Sexual Desire Disorder, International Society for the Study of Womens Sexual Health (ISSWSH) annual meeting, 2007, 2 pgs. (abstract).
Van Lundsen, Validation of the Sexual Interest and Desire Inventory-Female (SIDI-F) in European women, ISSWSH, 2007, 2 pgs. (abstract).

Goldfischer et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (abstract).
Krychman et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 6 pgs. (poster and oral presentation).
Clayton et al., Baseline Characteristics of Patients Enrolled in Three Phase III North American Trials of Flibanserin in Premenopausal Women With Hypoactive Sexual Desire Disorder, FIGO 2009, Oct. 2009, 1 pg., Cape Town, South Africa. (abstract).
Scandroglio et al., Ex Vivo binding of Flibanserin to Serotonin-5-HT1A and 5-HT2A Receptors, Pharm. Res., 2001, 43(2):179-183.
D'Aquila et al., Anti-anhedonic actions of the novel serotonergic agent flibanserin, a potential rapidly-acting antidepressant, Euro. J. Pharm., 1997, 340:121-132.
Flik et al., Assessment of serotonin and catecholamine levels in the female rat brain following acute and chronic administration with flibanserin, a potential novel treatment for hypoactive sexual desire disorder: an in vivo microdialysis study, presented at Neuroscience 2009, Feb. 3, 2010, http://www.abstractsonline.com/Plan/AbstractPrintView.aspx?mID=2285&sKey=65206 . . . , 2 pgs.
Banfi et al., Benzimidazolone Derivatives: a new class of putative antidepressant agents, 13th Int. Symp. On Medicinal Chemistry, Sep. 19-23, 1994, p. 102. (abstract).
Borsini et la., BIMT 17, a 5-HT1A receptor agonist/5-HT2A receptor antagonist, directly activates portsynaptic 5-HT inhibitory responses in the rat cerebral cortex, Naunyn-Schmiedeberg's Arch Pharm., 1995, 352:283-290.
Boehringer Ingelheim, Flibanserin BIMT-17, Drugs of the Future, 1999, 24(1):91.
Podhorna et al., Flibanserin has anxiolytic effects without locomotor side effects in the infant rat ultrasonic vocalization model of anxiety, Workshop on Depression Anxiety Spectrum Disorders: from Neurobiology to Novel Pharm. Treatmts, Int. Acad. for Biomed. and Drug Res., Abstract-Book, Milan, Jun. 7, 2000, 1 pg.
Vaccarino et al., Flibanserin, a 5-HT1A agonist/5-HT2A antagonist, decreases sucrose intake in operant and non-operant paradigms in rats, Soc. Neurosci. Abstr., 2000, 26:394:Abstr 144.9, 30th Ann. Mtg. of Soc. For Neurosci, New Orleans, Nov. 4-9, 1000, 1 pg.
Borsini et al., Further characterisation of potential antidepressant action of flibanserin, Psychopharm., 2001, 159:64-69.
Rueter et al., In Vivo Electrophysiological Assessment of the Agonistic Properties of Flibanserin at Pre- and Postsynaptic 5-HT1A Receptors in the Rat Brain, Synapse, 1998, 29:392-405.
Cervo et al., Involvement of 5-HT1A receptors in flibanserin discriminative stimulus in female rats, Neurosci 2009, Feb. 3, 2010, http://www.abstractsonline.com/Plan/AbstratPrintView.aspx?mID=2285&sKey=65206 . . . , 2pgs.
Cervo et al., Involvement of 5-HT1A receptors in flibanserin discriminative stimulus in female rats, Dept. CNS Diseases, Prog. No. 465.20, 2009 Neurosci., Oct. 19, 2009, 1 pg. (poster).
Ferger et al., Neurochemical characterization of Flibanserin a phase III drug for treatment of hypoactive sexual desire disorder (HSDD) in women, Neurosci 2009, Feb. 3, 2010, http://www.abstractsonline.com/Plan/AbstractPrintView.aspx?mIK=2285&sKey=65206 . . . , 2pgs.
Flik et al., Assessment of serotonin and catecholamine levels in the female rat brain following acute and chronic administration with flibanserin, a potential novel treatment for hypoactive sexual desire disorder: An in vivo microdialysis study, SFN, 2009, 1 pg. (poster).
Ferger et al., Neurochemical characterization of Flibanserin a phase III drug for treatment of hypoactive sexual desire disorder (HSDD) in women, SFN, 2009, 1 pg. (poster).
Evans et al., The Effects of Flibanserin on Amphetamine Withdrawal-Induced hypolocomotion in Rats, Soc. Neurosci Abstr., Nov. 7-12, 1998, 24:2133:Abstr 848.5, 28th Ann. Mtg. of the Soc. For Neurosci, Los Angeles, 1 pg.
Advisory Action dated Dec. 27, 2005, U.S. Appl. No. 10/272,603, filed Oct. 16, 2002 now U.S. Pat. No. 7,151,103, issued Dec. 19, 2006, 3 pgs.

(56) References Cited

OTHER PUBLICATIONS

Examiner's Interview dated Jun. 23, 2006, U.S. Appl. No. 10/272,603, filed Oct. 16, 2002 now U.S. Pat. No. 7,151,103, issued Dec. 19, 2006, 2 pgs.
Examiner's Interview dated Oct. 20, 2005, U.S. Appl. No. 10/272,603, filed Oct. 16, 2002 now U.S. Pat. No. 7,151,103, issued Dec. 19, 2006, 1 pg.
Final Office Action dated Jun. 2, 2005, U.S. Appl. No. 10/272,603, filed Oct. 16, 2002 now U.S. Pat. No. 7,151,103, issued Dec. 19, 2006, 9 pgs.
Notice of Allowance dated Jun. 23, 2006, U.S. Appl. No. 10/272,603, filed Oct. 16, 2002 now U.S. Pat. No. 7,151,103, issued Dec. 19, 2006, 7 pgs.
Notice of Appeal/Amendment dated Nov. 8, 2005, U.S. Appl. No. 10/272,603, filed Oct. 16, 2002 now U.S. Pat. No. 7,151,103, issued Dec. 19, 2006, 9 pgs.
Office Action dated Oct. 14, 2004, U.S. Appl. No. 10/272,603, filed Oct. 16, 2002 now U.S. Pat. No. 7,151,103, issued Dec. 19, 2006, 8 pgs.
RCE/Supp. Amendment dated Jun. 8, 2006, U.S. Appl. No. 10/272,603, filed Oct. 16, 2002 now U.S. Pat. No. 7,151,103, issued Dec. 19, 2006, 29 pgs.
Reply dated Feb. 14, 2005, U.S. Appl. No. 10/272,603, filed Oct. 16, 2002 now U.S. Pat. No. 7,151,103, issued Dec. 19, 2006, 20 pgs.
Examiner's Search Strategy dated Jun. 20, 2006, U.S. Appl. No. 10/272,603, filed Oct. 16, 2002 now U.S. Pat. No. 7,151,103, issued Dec. 19, 2006, 2 pgs.
Examiner's Search Strategy dated Jun. 21, 2006, U.S. Appl. No. 10/272,603, filed Oct. 16, 2002 now U.S. Pat. No. 7,151,103, issued Dec. 19, 2006, 20 pgs.
Examiner's Search Strategy dated Sep. 22, 2004, U.S. Appl. No. 10/272,603, filed Oct. 16, 2002 now U.S. Pat. No. 7,151,103, issued Dec. 19, 2006, 83 pgs.
Examiner's Search Strategy dated Sep. 28, 2004, U.S. Appl. No. 10/272,603, filed Oct. 16, 2002 now U.S. Pat. No. 7,151,103, issued Dec. 19, 2006, 117 pgs.
Examiner's Search Strategy dated Sep. 29, 2004, U.S. Appl. No. 10/272,603, filed Oct. 16, 2002 now U.S. Pat. No. 7,151,103, issued Dec. 19, 2006, 1 pg.
Examiner's Search Strategy dated Oct. 14, 2004, U.S. Appl. No. 10/272,603, filed Oct. 16, 2002 now U.S. Pat. No. 7,151,103, issued Dec. 19, 2006, 3pgs.
Final Office Action dated Oct. 5, 2005, U.S. Appl. No. 10/210,474, filed Aug. 1, 2002 now U.S. Pat. No. 7,183,410, issued Feb. 27, 2007, 6 pgs.
Notice of Allowance dated Jan. 30, 2006, U.S. Appl. No. 10/210,474, filed Aug. 1, 2002 now U.S. Pat. No. 7,183,410, issued Feb. 27, 2007, 7 pgs.
Notice of Allowance dated Jul. 12, 2006, U.S. Appl. No. 10/210,474, filed Aug. 1, 2002 now U.S. Pat. No. 7,183,410, issued Feb. 27, 2007, 7 pgs.
Office Action dated Mar. 16, 2005, U.S. Appl. No. 10/210,474, filed Aug. 1, 2002 now U.S. Pat. No. 7,183,410, issued Feb. 27, 2007, 9 pgs.
Office Action dated Jul. 26, 2004, U.S. Appl. No. 10/210,474, filed Aug. 1, 2002 now U.S. Pat. No. 7,183,410, issued Feb. 27, 2007, 7 pgs.
Response to Final Office Action dated Dec. 15, 2005, U.S. Appl. No. 10/210,474, filed Aug. 1, 2002 now U.S. Pat. No. 7,183,410, issued Feb. 27, 2007, 9 pgs.
Reply dated Jan. 26, 2005, U.S. Appl. No. 10/210,474, filed Aug. 1, 2002 now U.S. Pat. No. 7,183,410, issued Feb. 27, 2007, 24 pgs.
Amendment dated Jul. 11, 2005, U.S. Appl. No. 10/210,474, filed Aug. 1, 2002 now U.S. Pat. No. 7,183,410, issued Feb. 27, 2007, 13 pgs.
Examiner's Search Strategy dated Mar. 10, 2005, U.S. Appl. No. 10/210,474, filed Aug. 1, 2002 now U.S. Pat. No. 7,183,410, issued Feb. 27, 2007, 36 pgs.
Examiner's Search Strategy dated Sep. 30, 2005, U.S. Appl. No. 10/210,474, filed Aug. 1, 2002 now U.S. Pat. No. 7,183,410, issued Feb. 27, 2007, 6 pgs.
Reply with Amendment dated Mar. 8, 2005, U.S. Appl. No. 10/210,474, filed Aug. 1, 2002 now U.S. Pat. No. 7,183,410, issued Feb. 27, 2007, 10 pgs.
Supplemental Amendment dated Jan. 19, 2006, U.S. Appl. No. 10/210,474, filed Aug. 1, 2002 now U.S. Pat. No. 7,183,410, issued Feb. 27, 2007, 6 pgs.
Examiner's Interview dated Nov. 19, 2007, U.S. Appl. No. 11/546,303, filed Oct. 12, 2006, 3 pgs.
Final Office Action dated Sep. 14, 2007, U.S. Appl. No. 11/546,303, filed Oct. 12, 2006, 4 pgs.
Office Action dated Jan. 5, 2007, U.S. Appl. No. 11/546,303, filed Oct. 12, 2006, 7 pgs.
Response dated Jul. 5, 2007, U.S. Appl. No. 11/546,303, filed Oct. 12, 2006, 6 pgs.
Examiner's Search Strategy dated Mar. 10, 2005, U.S. Appl. No. 11/546,303, filed Oct. 12, 2006, 36 pgs.
Examiner's Interview Summ. dated Jan. 17, 2008, U.S. Appl. No. 11/546,304, filed Oct. 12, 2006 now U.S. Pat. No. 7,420,057 issued Sep. 2, 2008, 3 pgs.
Notice of Allowance dated Apr. 30, 2008, U.S. Appl. No. 11/546,304, filed Oct. 12, 2006 now U.S. Pat. No. 7,420,057 issued Sep. 2, 2008, 8 pgs.
Office Action dated Jan. 3, 2007, U.S. Appl. No. 11/546,304, filed Oct. 12, 2006 now U.S. Pat. No. 7,420,057 issued Sep. 2, 2008, 7 pgs.
Office Action dated Jul. 18, 2007, U.S. Appl. No. 11/546,304, filed Oct. 12, 2006 now U.S. Pat. No. 7,420,057 issued Sep. 2, 2008, 4 pgs.
Response dated Jan. 17, 2008, U.S. Appl. No. 11/546,304, filed Oct. 12, 2006 now U.S. Pat. No. 7,420,057 issued Sep. 2, 2008, 24 pgs.
Response dated Apr. 3, 2007, U.S. Appl. No. 11/546,304, filed Oct. 12, 2006 now U.S. Pat. No. 7,420,057 issued Sep. 2, 2008, 7 pgs.
Supp. Response dated Mar. 19, 2008, U.S. Appl. No. 11/546,304, filed Oct. 12, 2006 now U.S. Pat. No. 7,420,057 issued Sep. 2, 2008, 13 pgs.
Supp. Response dated Mar. 24, 2008, U.S. Appl. No. 11/546,304, filed Oct. 12, 2006 now U.S. Pat. No. 7,420,057 issued Sep. 2, 2008, 14 pgs.
2nd Supp. Response dated Apr. 23, 2008, U.S. Appl. No. 11/546,304, filed Oct. 12, 2006 now U.S. Pat. No. 7,420,057 issued Sep. 2, 2008, 14 pgs.
Final Office Action dated Apr. 23, 2007, U.S. Appl. No. 11/079,070, filed Mar. 14, 2005, 11 pgs.
Notice of Allowance dated Sep. 14, 2007, U.S. Appl. No. 11/079,070, filed Mar. 14, 2005, 6 pgs.
Office Action dated Jan. 11, 2008, U.S. Appl. No. 11/079,070, filed Mar. 14, 2005, 8 pgs.
Office Action dated Sep. 13, 2006, U.S. Appl. No. 11/079,070, filed Mar. 14, 2005, 5 pgs.
Response to Final Office Action dated Jul. 23, 2007, U.S. Appl. No. 11/079,070, filed Mar. 14, 2005, 7 pgs.
RCE dated Nov. 2, 2007, U.S. Appl. No. 11/079,070, filed Mar. 14, 2005, 4 pgs.
Response dated Jan. 16, 2007, U.S. Appl. No. 11/079,070, filed Mar. 14, 2005, 8 pgs.
Examiner Search Strategy dated Jan. 3, 2008, U.S. Appl. No. 11/079,070, filed Mar. 14, 2005, 20 pgs.
Examiner's Search Strategy dated Jul. 21, 2006, U.S. Appl. No. 11/079,070, filed Mar. 14, 2005, 106 pgs.
Advisory Action dated Jul. 2, 2009, U.S. Appl. No. 11/278,551, filed Apr. 4, 2006, 3 pgs.
Final Office Action dated Apr. 13, 2009, U.S. Appl. No. 11/278,551, filed Apr. 4, 2006, 9 pgs.
Office Action dated Jun. 1, 2007, U.S. Appl. No. 11/278,551, filed Apr. 4, 2006, 9 pgs.
Office Action dated Jul. 6, 2006, U.S. Appl. No. 11/278,551, filed Apr. 4, 2006, 8 pgs.
Office Action dated Jul. 9, 2008, U.S. Appl. No. 11/278,551, filed Apr. 4, 2006, 12 pgs.

(56) References Cited

OTHER PUBLICATIONS

Office Action dated Dec. 28, 2009, U.S. Appl. No. 11/278,551, filed Apr. 4, 2006, 9 pgs.
Responsive Amendment to Final Office Action, dated Jun. 12, 2009, U.S. Appl. No. 11/278,551, filed Apr. 4, 2006, 63 pgs.
RCE and Responsive Amendment to Final Office Action, dated Oct. 7, 2009, U.S. Appl. No. 11/278,551, filed Apr. 4, 2006, 14 pgs.
Response dated Jan. 9, 2009, U.S. Appl. No. 11/278,551, filed Apr. 4, 2006, 64 pgs.
Response dated Nov. 30, 2007, U.S. Appl. No. 11/278,551, filed Apr. 4, 2006, 25 pgs.
Response dated Dec. 19, 2006, U.S. Appl. No. 11/278,551, filed Apr. 4, 2006, 4 pgs.
Examiner's Search Strategy dated Apr. 13, 2009, U.S. Appl. No. 11/278,551, filed Apr. 4, 2006, 2 pgs.
Examiner's Search Strategy dated Jun. 1, 2007, U.S. Appl. No. 11/278,551, filed Apr. 4, 2006, 10 pgs.
Examiner's Search Strategy dated Jun. 26, 2006, U.S. Appl. No. 11/278,551, filed Apr. 4, 2006, 19 pgs.
Examiner's Search Strategy dated Jul. 9, 2008, U.S. Appl. No. 11/278,551, filed Apr. 4, 2006, 6 pgs.
Examiner's Search Strategy dated Dec. 28, 2009, U.S. Appl. No. 11/278,551, filed Apr. 4, 2006, 3 pgs.
Final Office Action dated Sep. 12, 2008, U.S. Appl. No. 11/381,590, filed Apr. 4, 2006, 10 pgs.
Office Action dated Apr. 3, 2007, U.S. Appl. No. 11/381,590, filed Apr. 4, 2006, 8 pgs.
Office Action dated Dec. 27, 2007, U.S. Appl. No. 11/381,590, filed Apr. 4, 2006, 8 pgs.
Response dated Jun. 26, 2008, U.S. Appl. No. 11/381,590, filed Apr. 4, 2006, 7 pgs.
Amendment and Reply dated Oct. 3, 2007, U.S. Appl. No. 11/381,590, filed Apr. 4, 2006, 8 pgs.
Examiner's Search Strategy dated Mar. 30, 2007, U.S. Appl. No. 11/381,590, filed Apr. 4, 2006, 48 pgs.
Office Action dated Mar. 23, 2009, U.S. Appl. No. 11/383,796, filed May 17, 2006; 11 pgs.
Examiner's Search Strategy dated Mar. 23, 2009, U.S. Appl. No. 11/383,796, filed May 17, 2006; 2 pgs.
Office Action dated Mar. 19, 2009, U.S. Appl. No. 11/383,793, filed May 17, 2006, 12 pgs.
Examiner's Search Strategy dated Mar. 19, 2009, U.S. Appl. No. 11/383,793, filed May 17, 2006, 3 pgs.
Advisory Action dated Feb. 10, 2009, U.S. Appl. No. 11/381,130, filed May 2, 2006, 3 pgs.
Final Office Action dated Jul. 18, 2008, U.S. Appl. No. 11/381,130, filed May 2, 2006, 17pgs.
Office Action dated Oct. 9, 2007, U.S. Appl. No. 11/381,130, filed May 2, 2006, 13 pgs.
Response to Final Office Action dated Jan. 21, 2009, U.S. Appl. No. 11/381,130, filed May 2, 2006, 13 pgs.
Response dated Apr. 9, 2008, U.S. Appl. No. 11/381,130, filed May 2, 2006, 36 pgs.
Office Action dated Jun. 1, 2009, U.S. Appl. No. 11/364,306, filed Feb. 28, 2006, 18 pgs.
Examiner's Search Strategy dated Jun. 1, 2009, U.S. Appl. No. 11/364,306, 3 pgs.
Final Office Action dated Sep. 4, 2008, U.S. Appl. No. 11/364,153, filed Feb. 28, 2006, 12 pgs.
Office Action dated Nov. 29, 2007, U.S. Appl. No. 11/364,153, filed Feb. 28, 2006, 11 pgs.
Response dated May 29, 2008, U.S. Appl. No. 11/364,153, filed Feb. 28, 2006, 62 pgs.
Office Action dated Apr. 29, 2009, U.S. Appl. No. 11/364,785, filed Feb. 28, 2006, 23 pgs.
Examiner's Search Strategy dated Apr. 29, 2009, U.S. Appl. No. 11/364,785, filed Feb. 28, 2006, 19 pgs.
Office Action dated Apr. 9, 2009, U.S. Appl. No. 12/170,884, filed Jul. 10, 2008, 10 pgs.
Response dated Oct. 9, 2009, U.S. Appl. No. 12/170,884, filed Jul. 10, 2008, 3 pgs.
Examiner's Search Strategy dated Feb. 19, 2010, U.S. Appl. No. 12/170,884, filed Jul. 10, 2008, 26 pgs.
Examiner's Interview Summary dated Feb. 19, 2010, U.S. Appl. No. 12/170,884, filed Jul. 10, 2008, 4 pgs.
Notice of Allowance dated Feb. 19, 2010, U.S. Appl. No. 12/170,884, filed Jul. 10, 2008, 5 pgs.
Office Action dated Mar. 5, 2009, U.S. Appl. No. 11/740,959, filed Apr. 27, 2007, 30 pgs.
Response dated Sep. 3, 2009, U.S. Appl. No. 11/740,959, filed Apr. 27, 2007, 12 pgs.
Examiner's Search Strategy dated Mar. 5, 2009, U.S. Appl. No. 11/740,959, filed Apr. 27, 2007, 12 pgs.
Final Office Action dated Jan. 20, 2010; U.S. Appl. No. 11/740,959, filed Apr. 27, 2007, 33 pgs.
Examiner's Search Strategy dated Jan. 20, 2010, U.S. Appl. No. 11/740,959, filed Apr. 27, 2007, 6 pgs.
Office Action dated Apr. 13, 2009, U.S. Appl. No. 11/097,939, filed Apr. 4, 2005, 12 pgs.
Amendment and Response dated Sep. 14, 2009, U.S. Appl. No. 11/097,939, filed Apr. 4, 2005, 8 pgs.
Examiner's Search Strategy dated Apr. 13, 2009, U.S. Appl. No. 11/097,939, filed Apr. 4, 2005, 3 pgs.
Final Office Action dated Feb. 17, 2010, U.S. Appl. No. 11/097,939, filed Apr. 4, 2005, 16 pgs.
Examiner's Search Strategy dated Feb. 17, 2010, U.S. Appl. No. 11/097,939, filed Apr. 4, 2005, 2 pgs.
Office Action dated Mar. 19, 2009, U.S. Appl. No. 11/554,855, filed Oct. 31, 2006, 11 pgs.
Response dated Aug. 19, 2009, U.S. Appl. No. 11/554,855, filed Oct. 31, 2006, 7 pgs.
Examiner's Search Strategy dated Mar. 19, 2009, U.S. Appl. No. 11/554,855, filed Oct. 31, 2006, 3 pgs.
Office Action dated Dec. 4, 2009, U.S. Appl. No. 11/554,855, filed Oct. 31, 2006, 15 pgs.
Examiner's Search Strategy dated Dec. 4, 2009, U.S. Appl. No. 11/554,855, filed Oct. 31, 2006, 3 pgs.
Office Action dated Mar. 19, 2009, U.S. Appl. No. 11/745,515, filed May 8, 2007, 11 pgs.
Office Action dated Dec. 4, 2009, U.S. Appl. No. 11/745,515, filed May 8, 2007, 16 pgs.
Examiner's Search Strategy dated Mar. 19, 2009, U.S. Appl. No. 11/745,515, filed May 8, 2007, 3 pgs.
Response dated Aug. 19, 2009, U.S. Appl. No. 11/745,515, filed May 8, 2007, 8 pgs.
Examiner's Search Strategy dated Dec. 4, 2009, U.S. Appl. No. 11/745,515, filed May 8, 2007, 3 pgs.
Office Action dated Oct. 11, 2005, U.S. Appl. No. 10/882,613, filed Jul. 1, 2004, 7 pgs.
Examiner's Search Strategy dated Oct. 2, 2005, U.S. Appl. No. 10/882,613, filed Jul. 1, 2004, 17 pgs.
Advisory Action dated Mar. 16, 2007, U.S. Appl. No. 10/444,892, filed May 22, 2003, 2 pgs.
Advisory Action dated Mar. 29, 2007, U.S. Appl. No. 10/444,892, filed May 22, 2003, 3 pgs.
Examiner's Interview Summ. dated Oct. 4, 2007, U.S. Appl. No. 10/444,892, filed May 22, 2003, 2 pgs.
Final Office Action dated Aug. 29, 2006, U.S. Appl. No. 10/444,892, filed May 22, 2003, 7 pgs.
Office Action dated Mar. 1, 2006, U.S. Appl. No. 10/444,892, filed May 22, 2003, 5 pgs.
Amendment After Final dated Feb. 28, 2007, U.S. Appl. No. 10/444,892, filed May 22, 2003, 8 pgs.
Amendment dated Jun. 27, 2006, U.S. Appl. No. 10/444,892, filed May 22, 2003, 5 pgs.
Office Action dated Jul. 2, 2007, U.S. Appl. No. 11/110,449, filed Apr. 20, 2005, 11 pgs.
Examiner's Search Strategy dated Jun. 20, 2007, U.S. Appl. No. 11/110,449, filed Apr. 20, 2005, 7 pgs.
Office Action dated Jun. 29, 2009, U.S. Appl. No. 11/960,957, filed Oct. 20, 2007, 12 pgs.

(56) References Cited

OTHER PUBLICATIONS

Response dated Dec. 29, 2009, U.S. Appl. No. 11/960,957, filed Oct. 20, 2007, 10 pgs.
Examiner's Search Strategy dated Jun. 29, 2009, U.S. Appl. No. 11/960,957, filed Oct. 20, 2007, 1 pgs.
Notice of Non-Compliant Amendment dated Mar. 10, 2010, U.S. Appl. No. 11/960,957, filed Oct. 20, 2007, 2 pgs.
Amendment and Response to Notice of Non-Compliant Amendment dated Apr. 9, 2010, U.S. Appl. No. 11/960,957, filed Oct. 20, 2007, 5 pgs.
Office Action dated Jan. 26, 2007, U.S. Appl. No. 11/178,716, filed Jul. 11, 2005, 8 pgs.
Office Action dated Apr. 14, 2006, U.S. Appl. No. 11/178,716, filed Jul. 11, 2005, 8 pgs.
Amendment dated Jul. 25, 2006, U.S. Appl. No. 11/178,716, filed Jul. 11, 2005, 5 pgs.
Examiner's Search Strategy dated Jan. 21, 2007, U.S. Appl. No. 11/178,716, filed Jul. 11, 2005, 1 pg.
Examiner's Search Strategy dated Mar. 30, 2006, U.S. Appl. No. 11/178,716, filed Jul. 11, 2005, 15 pgs.
Examiner's Search Strategy dated Apr. 11, 2006, U.S. Appl. No. 11/178,716, filed Jul. 11, 2005, 1 pg.
Final Office Action dated May 18, 2007, U.S. Appl. No. 11/218,107, filed Sep. 1, 2005, 11 pgs.
Office Action dated Aug. 15, 2006, U.S. Appl. No. 11/218,107, filed Sep. 1, 2005, 8 pgs.
Response dated Feb. 14, 2007, U.S. Appl. No. 11/218,107, filed Sep. 1, 2005, 4 pgs.
Examiner's Search Strategy dated Jun. 30, 2006, U.S. Appl. No. 11/218,107, filed Sep. 1, 2005, 8 pgs.
Examiner's Search Strategy dated Aug. 11, 2006, U.S. Appl. No. 11/218,107, filed Sep. 1, 2005, 2 pgs.
Office Action dated Aug. 26, 2008, U.S. Appl. No. 11/940,655, filed Nov. 15, 2007, 7 pgs.
Office Action dated Sep. 28, 2009, U.S. Appl. No. 11/997,567, filed Mar. 21, 2008, 7 pgs.
Examiner's Search Strategy dated Sep. 28, 2009, U.S. Appl. No. 11/997,567, filed Mar. 21, 2008, 43 pgs.
Response dated Feb. 19, 2010, U.S. Appl. No. 11/997,567, filed Mar. 21, 2008, 10 pgs.
Office Action dated Jan. 25, 2010, U.S. Appl. No. 11/837,957, filed Aug. 13, 2007, 11 pgs.
Examiner's Search Strategy dated Jan. 25, 2010, U.S. Appl. No. 11/837,957, 6 pgs.
Examiner's Interview Summ. dated Oct. 2, 2009, U.S. Appl. No. 11/837,959, filed Aug. 13, 2007, 2 pgs.
Office Action dated Jul. 20, 2009, U.S. Appl. No. 11/837,959, filed Aug. 13, 2007, 8 pgs.
Examiner's Search Strategy dated Jul. 20, 2009, U.S. Appl. No. 11/837,959, filed Aug. 13, 2007, 5 pgs.
Final Office Action dated Mar. 25, 2010, U.S. Appl. No. 11/837,959, filed Aug. 13, 2007, 12 pgs.
Response dated Jan. 20, 2010, U.S. Appl. No. 11/837,959, filed Aug. 13, 2007, 11 pgs.
Ferger et al., Flibanserin, a drug intended for treatment of hypoactive sexual desire disorder in pre-menopausal women, affects spontaneous motor activity and brain neurochemistry in female rates, Naunyn Schmiedebergs Arch Pharmacol., Apr. 27, 2010, pp. 1-17 (epub ahead of print).
Aubert et al., Comparison of Flibanserin With the 5-Htla Agonist (+)-8-Oh-Dpat in Affecting Interactions Between Male-Female Marmoset Pairs, J. Sex Med., May 2010, 7(s3):118. (abstract).
Aubert et al., Initial PET Assessment of Flibanserin-induced Neural Changes in Female Marmoset Monkeys, J. Sex Med., May 2010, 7(s3):131. (abstract).
Aubert et al., Chronic Treatment of Female Marmoset Monkeys with (+)-8-OH-DPAT or Flibanserin Differentially Alters Response of the Hypothalamic-Pituitary-Adrenal Axis to Restraint and Acute Serotonergic Challenge, J. Sex Med., May 2010, 7(s3):131. (abstract).
Gelez et al., Chronic Flibanserin Treatment Increases Solicitations in the Female Rat, J. Sex Med., May 2010, 7(s3):118. (abstract).
Allers et al., Acute and Repeated Flibanserin Administration in Female Rats Modulates Monoamines Differentially Across Brain Areas: A Microdialysis Study, J. Sex Med., Feb. 2010, 33 pgs. (Epub ahead of print).
Goldfischer et al., Efficacy of Continued Flibanserin Treatment on Sexual Desire, Satisfying Sexual Events and Sexual Functioning in Premenopausal Women With HSDD: Results From the Researching Outcomes on Sustained Efficacy (ROSE) Study, International Society for the Study of Womens Sexual Health (ISSWSH) annual meeting, 2008, 17 pgs. (oral presentation).
Final Office Action dated May 21, 2010, U.S. Appl. No. 11/997,567, filed Mar. 21, 2008, 7 pgs.
Final Office Action dated May 27, 2010, U.S. Appl. No. 11/278,551, filed Apr. 4, 2006, 8 pgs.
Examiner's Search Strategy dated May 27, 2010, U.S. Appl. No. 11/278,551, filed Apr. 4, 2006, 3 pgs.
Response dated Jun. 4, 2010, U.S. Appl. No. 11/554,855, filed Oct. 31, 2006, 10 pgs.
Response dated Jun. 4, 2010, U.S. Appl. No. 11/745,515, filed May 8, 2007, 8 pgs.
Restriction Requirement dated May 24, 2004, U.S. Appl. No. 10/210,474, filed Aug. 1, 2002 now U.S. Pat. No. 7,183,410, issued Feb. 27, 2007, 6 pgs.
Response to Restriction Requirement dated Jun. 9, 2004 U.S. Appl. No. 10/210,474, filed Aug. 1, 2002 now U.S. Pat. No. 7,183,410, issued Feb. 27, 2007, 2 pgs.
Restriction Requirement dated Aug. 20, 2008, U.S. Appl. No. 11/097,939, filed Apr. 4, 2005, 8 pgs.
Response to Restriction Requirement dated Feb. 12, 2009, U.S. Appl. No. 11/097,939, filed Apr. 4, 2005, 2 pgs.
Restriction Requirement dated Feb. 8, 2007, U.S. Appl. No. 11/110,449, filed Apr. 20, 2005, 8 pgs.
Response to Restriction Requirement dated Jun. 7, 2007, U.S. Appl. No. 11/110,449, filed Apr. 20, 2005, 2 pgs.
Restriction Requirement dated Dec. 23, 2008, U.S. Appl. No. 11/187,422, filed Jul. 22, 2005, 11 pgs.
Restriction Requirement dated May 23, 2007, U.S. Appl. No. 11/364,153, filed Feb. 28, 2006, 7 pgs.
Response to Restriction Requirement dated Sep. 24, 2007, U.S. Appl. No. 11/364,153, filed Feb. 28, 2006, 2 pgs.
Restriction Requirement dated Dec. 18, 2006, U.S. Appl. No. 11/381,590, filed Apr. 4, 2006, 7 pgs.
Response to Restriction Requirement dated Mar. 9, 2007, U.S. Appl. No. 11/381,590, filed Apr. 4, 2006, 2 pgs.
Restriction Requirment dated Aug. 18, 2008; U.S. Appl. No. 11/740,959, filed Apr. 27, 2007, 9 pgs.
Response to Restriction Requirment dated Nov. 18, 2008; U.S. Appl. No. 11/740,959, filed Apr. 27, 2007, 6 pgs.
Restriction Requirement dated Aug. 21, 2009, U.S. Appl. No. 11/837,957, filed Aug. 13, 2007, 7 pgs.
Response to Restriction Requirement dated Sep. 21, 2009, U.S. Appl. No. 11/837,957, filed Aug. 13, 2007, 2 pgs.
Restriction Requirement dated Jun. 21, 2010, U.S. Appl. No. 11/956,949, filed Dec. 14, 2007, 7 pgs.
Restriction Requirement dated Feb. 5, 2009, U.S. Appl. No. 11/960,957, filed Oct. 20, 2007, 8 pgs.
Response to Restriction Requirement dated Mar. 4, 2009, U.S. Appl. No. 11/960,957, filed Oct. 20, 2007, 2 pgs.
Restriction Requirement dated Jun. 30, 2009, U.S. Appl. No. 11/997,567, filed Mar. 21, 2008, 7 pgs.
Response to Restriction Requirement dated Jul. 23, 2009, U.S. Appl. No. 11/997,567, filed Mar. 21, 2008, 2 pgs.
Restriction Requirement dated May 4, 2010, U.S. Appl. No. 12/279,589, filed Sep. 26, 2008, 9 pgs.
RCE dated May 19, 2010, U.S. Appl. No. 12/170,884, filed Jul. 10, 2008, 3 pgs.
Examiner's Interview dated Apr. 15, 2009, U.S. Appl. No. 11/524,268, filed Sep. 21, 2006, 4pgs.
Examiner's Interview dated Oct. 23, 2007, U.S. Appl. No. 11/524,268, filed Sep. 21, 2006, 1 pg.

(56) References Cited

OTHER PUBLICATIONS

Notice of Allowance dated Jan. 11, 2010, U.S. Appl. No. 11/524,268, filed Sep. 21, 2006, 7 pgs.
Office Action dated Feb. 11, 2008, U.S. Appl. No. 11/524,268, filed Sep. 21, 2006, 15 pgs.
Office Action dated May 2, 2007, U.S. Appl. No. 11/524,268, filed Sep. 21, 2006, 10 pgs.
Office Action dated Dec. 1, 2008, U.S. Appl. No. 11/524,268, filed Sep. 21, 2006, 16 pgs.
Amendment dated Jun. 1, 2009, U.S. Appl. No. 11/524,268, filed Sep. 21, 2006, 64 pgs.
Response dated Aug. 11, 2008, U.S. Appl. No. 11/524,268, filed Sep. 21, 2006, 15 pgs.
Response dated Nov. 2, 2007, U.S. Appl. No. 11/524,268, filed Sep. 21, 2006, 32 pgs.
Examiner's Search Strategy dated Jan. 11, 2010, U.S. Appl. No. 11/524,268, filed Sep. 21, 2006, 5 pgs.
Examiner's Search Strategy dated Dec. 1, 2008, U.S. Appl. No. 11/524,268, filed Sep. 21, 2006, 4 pgs.
RCE dated Apr. 9, 2010, U.S. Appl. No. 11/524,268, filed Sep. 21, 2006, 2 pgs.
Office Action dated Jan. 11, 2010, U.S. Appl. No. 11/837,962, filed Aug. 13, 2007, 17 pgs.
Examiner's Search Strategy dated Jan. 11, 2010, U.S. Appl. No. 11/837,962, filed Aug. 13, 2007, 8 pgs.
Response dated Jun. 11, 2010 U.S. Appl. No. 11/837,962, filed Aug. 13, 2007, 16 pgs.
Restriction Requirement dated Sep. 9, 2009, U.S. Appl. No. 11/837,962, filed Aug. 13, 2007, 10 pgs.
Response to Restriction Requirement dated Sep. 25, 2009, U.S. Appl. No. 11/837,962, filed Aug. 13, 2007, 2 pgs.
Office Action dated Jan. 14, 2010, U.S. Appl. No. 12/091,848, filed Apr. 28, 2008, 5 pgs.
Examiner's Search Strategy dated Jan. 14, 2010, U.S. Appl. No. 12/091,848, filed Apr. 28, 2008, 47 pgs.
Response dated Jun. 14, 2010 U.S. Appl. No. 12/091,848, filed Apr. 28, 2008, 5 pgs.
Restriction Requirement dated Oct. 7, 2009, U.S. Appl. No. 12/091,848, filed Apr. 28, 2008, 5 pgs.
Response to Restriction Requirement dated Nov. 9, 2009, U.S. Appl. No. 12/091,848, filed Apr. 28, 2008, 9 pgs.
Notice of Non-Compliant Amendment dated Jun. 22, 2010 U.S. Appl. No. 12/091,848, filed Apr. 28, 2008, 2 pgs.
Response to Notice of Non-Compliant Amdmt dated Jun. 23, 2010 U.S. Appl. No. 12/091,848, filed Apr. 28, 2008, 6 pgs.
Final Office Action dated Jul. 9, 2010; U.S. Appl. No. 11/960,957, filed Dec. 20, 2007, 9 pgs.
U.S. Appl. No. 08/039,002, filed Mar. 25, 1993, Bietti.
U.S. Appl. No. 11/956,949, filed Dec. 14, 2007, Lewis-D'Agostino, et al.
U.S. Appl. No. 12/390,665, filed Feb. 23, 2009, Wunderlich, et al.
U.S. Appl. No. 12/532,269, filed Dec. 14, 2009, Boeck, et al.
U.S. Appl. No. 12/675,231, filed Feb. 25, 2010, Hanes, et al.
Aizenberg et al., Cyproheptadine Treatment of Sexual Dysfunction Induced by Serotonin Reuptake Inhibitors, Clinical Neuropharmacology, 18(4):320-324, 1995 Lippincott-Raven Publishers, Philadelphia.
Anonymous, Hormone Patch may Provide Some Increase in Sexual Desire in Menopausal Women, Jul. 25, 2005, URL:http://pubs.ama-assn.org/media/2005a/0725.dtl, 2 pgs.
Archer, 5-HT, Pain and aniety, Behavioural Pharmacology of 5-HT, 1989, pp. 299-300.
Awouters et al., Chemical Abstract 88-98788c, Apr. 10, 1978, 2 pgs.
Backhauss et al., A Mouse Model of Focal Cerebral Ischemia for Screening Neuroprotective Drug Effects, J of Pharm Methods, 1992, 27:27-32.
Basson et al., Report of the international consensus development conference on female sexual dysfunction: definitions and classifications; J of Urology; Mar. 2000, 163:888-893.

Baxter et al., 5-HT2 Receptor Subtypes: A Family Re-United?, Trends in Pharm Sci, Mar. 1995, 16(3):105-110 (on ISR for 1/1872) Elsevier, Haywarth, GB.
Bechard, et al., Int. J. Pharm., 1992, 87:133-139.
Beers et al; The Merck Manual of Diagnosis and Therapy; Editor in Chief, 17th Ed. 1999, pp. 1595-1598.
Bernstein et al., Concomitant Polymorphs, Angewandte Chemie, Int. Ed., 1999, pp. 3441-3461.
Bevan et al, 5-HT and sexual behaviour, Behav Pharm of 5-HT, 1989, pp. 33-34, 87-88.
Borsini et al, Behavioral Effects of Flibanserin (BIMT 17), Pharm, Biochem and Behavior, Sep. 1999, 64(1):137-146.
Borsini et al; Flibanserin, Prop INN, BIMT 17, 1,3-Dihydro-1-[2-[4-[3[(trifluoromethyl)phenyl]-1-piperazinyl]-22h-benzimidazol-2-one, Drugs of the future, 1998, 23(1):9-16.
Borsini et al., BIMT 17, a 5-HT2A receptor antagonist and 5-HT1A receptor full agonist in rat cerebral cortex, Naunyn-Schmiedeberg's Archives of Pharm., 1995, 352(3):276-282.
Borsini et la., Lack of interaction between flibanserin and antidepressants in inducing serotonergic syndrome in rats, Intl J Neuropsychopharmacology, 2001, 4(1):9-15, University Press, Cambridge, GB.
Borsini et al., Mechanism of action of flibanserin in the learned helplessness paradigm in rats, Euro J Pharm, 2001, 433:81-89.
Borsini, et al., Pharmacology of Flibanserin, CNS Drug Reviews, 2002; 8(2):117-142.
Borsini et al., BIMT 17: a putative antidepressant with a fast onset of action?, Psychopharmacology, 1997, 134:378-386.
Braiman, Psychosexual disorders of young adulthood, Clin Obstetrics and Gynecology, 1970, 13(3):734-745.
Brambilla et al., Effect of Flibanserin (BIMT 17), fluoxetine 8-OH-DPAT and busprione on serotonin synthesis in rat brain, Euro Neuropsychopharmacology, 1999, 10(1):63-67.
Buhrich, et al., Can fetishism occur in transexuals?, Arch Sex Behav, 1977, 6(3):223-235.
Butts, The relationship between sexual addiction and sexual dysfunction, J. Health Care Underserved, 1992, 3(1):128-35; discussion 136-7.
Buvat, et al., Role of hormones in sexual dysfunction, homosexuality, transsexualism, and paraphilia related disorders. Diagnostic and therapeutic consequences, Contracept Fertil Sex, 1996, 24(11):834-846-only English abstract.
Bymaster, et al., Fluoxetine, but not other selective serotonin uptake inhibitors, increases norepinephrine and dopamine extracellular levels in prefrontal cortex, Psychopharmacology, 2002, 160:353-361.
Byrn, et al., Hydrates and Solvates, Solid State Chemistry & Drugs, 1999, Chpt. 11, pp. 233-247.
Carey, Viagra for Women?, Business Week.com, www.businessweek.com/print/bwdaily/dnflash/content/dec2006/db20061228_31524 . . . , Jan. 12, 2007, 2 pgs. (citation from Hunton & Williams).
Cesana et al., The effect of BIMT 17, a new potential antidepressant, in the forced swimming test in mice, Behavioral Pharm, 1995, 6:688-694, Rapid Science Publishers, GB.
Chalmers et al., Corticotrophin-releasing factor receptors: from molecular biology to drug design, TiPS, Apr. 1996, 17:166-72.
Chiao, et al., Remington Pharm 19$^{th}$ Ed., Panamerican Spain, 1988, pp. 2535-2537.
Collino et al., Mannich bases of bensimidazoles, benzotriazoles and other analogous compounds, with pharmacological activity, Chem Abstr: Database accession No. 98:16650-XP 002197885, 1983: 16650, 1 pg.
Cloninger, A systematic method for clinical description and classification of personality variants, Arch. Gen. Psychiatry, Jun. 1987, 44:573-588.
Cools, Depression and psychosis, Behavioural Pharm of 5-HT, 1989, pp. 153-155.
Cooper, et al., A female sex offender with multiple paraphilias: a psychologic, physiol ogic (laboratory sexual arousal) and endocrine case study, Can J Psychiatry, 1990, 35(4):334-7.
Cremers et al., Non Erectile Dysfunction Application of Sildenafil, Herz, 2003, 28(4):325-333, XP002404204.

(56) References Cited

OTHER PUBLICATIONS

Crook et al., Effects of ondansertron in age-associated memory impairment, The role of ondansetron, a novel 5-HT3 antagonist, in the treatment of psychiatric disorders, 5th World Congress of Biochemical Psychiatry, 1991, pp. 21-23.

Cyr et al. Nefazodone: Its place among antidepressants, Annals of Pharmacotherapy, 1996, 30(9):1006-1012.

Damir et al., Hemodynamic effects of pharmacological block during acute overload of the heart Chemical Abstract, Database accession No. 1978:591197, Columbus 1978, XP-002436715.

Damour et al., Chemical Abstract, Mar. 29, 1993, 118(13):124537e.

Darlington, Flibanserin Boehringer Ingelheim Corp., Curr Opin in CPNS investigational drugs, 1999, 1(4):510-513, Pharma Press, London, GB.

De Vry, 5-HT1A receptors in psychopathology and the mechanism of action of clinically effective therapeutic agents, Drug News and Perspectives 1996, 9(5):270-280.

Deangelis, 5-HT2A antagonists in psychiatric disorders; Curr Opin in Investigational Drugs, 2002; 3(1):106-112; ISSN: 1472-4472.

Dimmock et al., Efficacy of selective serotonin-reuptake inhibitors in premenstrual syndrome: A systematic review, Lancet, Sep. 30, 2000, 356(9236):1131-36.

Fourcroy, Female sexual dysfunction: potential for pharmaotherapy, Drugs, 2003, 63(14):1445-1457.

Frampton et al, Pentoxifylline ( Oxpentifylline) A Review of its Therapeutic Efficacy in the Management of Peripheral Vascular and Cerebrovascular Disorders, Drug Evaluation—Drugs and Aging, 1995, 7(6):480-503.

Fujikura et al., Effects of naftidrofuryl oxalate, a 5-HT2 antagonist, on neuronal damage and local cerebral blood flow following transient cerebral ischemia in gerbils, Brain Research, 1994, 636:103-106.

Geyer, 5-HT2 antagonists increase tactile startle habituation in an animal model of habituation deficit in schizophrenia, Behavioural Pharm of 5-HT, 1989, pp. 243-246.

Giron, Thermal analysis and calorimetric methods in the characterisation of polymorphs and solvates, Thermochimica ACTA, 1995, 248:1-59, Elsevier Science.

Goa et al., Buspirone. A preliminary review of its pharmacological properties and therapeutic efficacy as an anxiolytic, Drugs, 1986, 32:114-129.

Gonzales, Natural Compound May Offer New Treatment for Chronic Pain, NIDA Notes, Aug. 2001, 16(3), www.nida.nih.gov/NIDA_Notes/ NNVol16N3/Natural.html , 2 pgs.

Gould, Salt selection for basic drugs, Intl J Pharmaceu, Nov. 1986, 33:201-217.

Grau, et al., Risk Factors, Outcome, and Treatment in Subtypes of Ischemic Stroke: The German Stroke Data Bank, Stroke, 2001; 32:2559-2566.

Greene, Protective groups in organic synthesis, Havard University, 1981, pp. 10-17, Wiley-Interscience Publication.

Guarraci, et al: Coffee, Tea and Me: Moderate doses of caffeine affect sexual behavior in female rats, Pharma Biochem and Behavior, Nov. 2005, 82(3):522-530. ISSN: 0091-3057 Elsevier, US, abstract.

Hansenne et al., Harm avoidance dimension of the tridimensional personality questionnaire and serotonin-1A activity in depressed patients, Biol. Psychiatry, 1997, 42:959-961.

Invernizzi et al., Flibanserin, a potential antidepressant drug, lowers 5-HT and raises dopamine and noradrenaline in the rat prefrontal cortex dialysate: role of 5-HT1A receptors, British J Pharm, Jun. 2003, 139:1281-1288.

Kafka, A Monoamine Hypothesis for the Pathophysiology of Paraphilic Disorders, Archives of Sex Behav, 1997, 26(4):343-58.

Kleven, Modification of behavioral effects of 8-hydroxy-2-(di-n-propylamino) tetralin following chronic ethanol consumption in the rat: evidence for the involvement of 5-HT1A receptors in ethanol dependence, Euro J Pharm, Aug. 15, 1995, 281(3):219-228.

Koba, Involvement of peripheral 5-HT2A receptor activation in pain behavior evoked by formalin paw injection in the rat, Kyushu Shika Gakkai Zaahi, 1999, abstract only, 1 pg.

Lammers et al., Ritanserin, a 5-HT2 receptor blocker, as add on treatment in narcolepsy, Sleep, 1991, 14(2):130-132.

Leonard, Sub-types of serotonin receptors: biochemical changes and pharmacological consequences, Intl Clin Psychopharmacology, 1992, 7:13-21.

Lyrer, Neue Ansatze in der Akutbehandlung des zerebrovaskularen Insultes (New Approaches in the Acute Treatment of Cerebrovascular Insult, 1994, 124(45):2005-2012, Schweiz. Med. Wochenschr. English translation attached.

Marazziti et al., Region-dependent effects of flibanserin and buspirone on adenylyl cyclase activity in the human brain, Intl J Neuropsychopharmacology, Jun. 2002, 5(2):131-140.

Marshall, et al., Unified Approach to the Analysis of Genetic Variation in Serotonergic Pathways, Am J. Med. Genetics Neurophychiatric Genetics, 1999, 88:621-627.

Martindale, Anxiolytic Sedatives Hypnotics and Antipsychotics, The Complete Drug Reference, 1999, p. 635, Pharmaceutial Press, London 32.

McCall et al., Role of serotonin 1A and serotonin 2 receptors in the central regulation of the cardiovascular system, Pharma Reviews, 1994, 46(3):231-243.

Merck Manual of Diagnosis and Therapy, 1999, 17th Ed, p. e 1410, col. 1, p. 1412, tables 173-2; p. 1413, col. 2, paragraph 1, Merck Research Laboratories, USA.

Merriam Webster New Collegiate Dictionary, definition of Diagnosis, 1981, p. 311.

Meston et al., Psychoactive Drugs and Human Sexual Behavior: The Role of Serotonergic Activity, J Psychoactive Drugs, Jan.-Mar. 1992, 24(1):1-40.

Miranda et al., Dexketoprofen-Induced antinociception in animal models of acute pain: Synergy with morphine and paracetamol, Neuropharmacology, 2007, 52:291-296.

Moser, Lust, lack of desire and paraphilias: some thoughts and possible connections, Marital Ther, 1992, 18(1):65-9.

Moynihan, The making of disease: female sexual dysfunction, British Med J, 2003, 326:45-47 XP-002416081.

Mutschler, et al., The Effect of Drugs: Antidepressive Agents, Manual of Pharmacology and Toxicology, 8th Ed, pp. 171-172, Scientific Publishing Company PLC, Stuttgart.

Nadeson et al., Antinociceptive role of 5-HT1A receptors in rat spinal cord, Lab Invest, British J Anaesthesia, 2002, 88(5):679-84.

Okamoto et al., 5-HT2A receptor subtype in the peripheral branch of sensory fibers is involved in the potentiation of inflammatory pain in rats, Pain, 2002, 99:133-143.

Otsuka, et al., Chem. Pharm. Bull., 1999, 47(6):852.856.

Petkov et al., Participation of differnet 5-HT receptors in the memory process in rats and its modulation by the serotonin depletorpchlorophenylalanine, Acta Neurobiol. Exp. 1995, 55:243-252.

Pharmacopia, 1995, p. 1843.

Phillips et al., Depression and Sexual Desire, American Family Physician, Aug. 15, 2000, 62(4).

Podhorna et al., Flibanserin has anxiolytic effects without locomotor side effects in the infant rat ultrasonic vocalization model of anxiety, British J Pharm, 2000, 130(4):739-746.

Prehn et al., Effects of serotonergic drugs in experimental brain ischemia: evidence for a protective role of serotonin in cerebral ischemia; Brain Research, 1993, 630:10-20.

Prehn et al., Neuroprotective properties of 5-HT1A receptor agonists in rodent models of focal and global cerebral ischemia; Euro J Pharm, 1991, 203:213-222.

Riekkinen et al., The effects of increased serotonergic and decreased cholinergic activities on spatial navigation performance in rats, Pharm Biochem & Behavior, 1991, 39:25-29.

Risch et al., Neurochemical alterations of serotonergic neuronal systems in depression, J Clin. Psychiatry, 1992, 53(10 Suppl.):3-7.

Robinson, Serotonin receptor subtypes and affective disorders, Clin Neuropharmacology, 1993, 16(S3):S1-S5.

Rosland et al., The formalin test in mice: effect of formalin concentration, Pain, 1990, 42:235-242.

(56) References Cited

OTHER PUBLICATIONS

Rueter et al., Electrophysiological examination of the effects of sustained flibanserin administration on serotonin receptors in rat brain, British J Pharm, 1999, 126(3):627-638.
Schwartz, et al., Conceptual factors in the treatment of paraphilias: a preliminary rep., Maritial Ther, 1983, 9(2):3-18.
Semkova, et al., Neuroprotective effect of 5-HT1A receptor agonist, Bay x 3702, demonstrated in vitro and in vivo, Euro J Pharm, 1998, 359:251-260.
Shibata et al., Ischemia-induced impairment of 2-deoxyglucose uptake and CA1 field potentials in rat hippocampal slices: protection by 5-HT1A receptor agonists and 5-HT2 receptor antagonists, Euro J Pharm, 1992, 229:21-29.
Shipton et al., Valvular heart disease: review and update, Am Family Phy, 2001, 63(11):2201-2208 XO-002436713.
Sietsema et al., From Taboo to Treatment?, Good Clin Prac, Jan. 2005, 12(1):23-27.
Singhal, et al., Advanced Drug Delivery Reviews, 2004, 56:335-347.
Soederberg, et al., Leptin Is a Risk Marker for First-Ever Hemorrhagic Stroke in a Population-Based Cohort, Stroke, J1 of the Am Heart Assoc., 1999; 30:328-337.
spine-health.com, Types of Back Pain: Acute Pain, Chronic Pain and Neuropathic Pain, www.spine-health.com/topics/cd/chronic_pain/chronicpain02.html, Oct. 2, 2007, 2 pgs.
Stedman's Medical Dictionary definition "Anxiety", 28$^{th}$ Ed., 2006, p. 114, Lippincott Williams & Wilkins, Baltimore MD.
Steiner, Recognition of Premenstrual Dysphoric Disorder and Its Treatmen, Lancet, Sep. 30, 2000, 356(9236):1126-27.
Thrombolytic Therapy: MedlinePlus Medical Encyclopedia, http://www.nlm.nih.gov/medlineplus/ency/article/007089.htm, accessed Dec. 17, 2009, pp. 1-4.
Vandenberk et al., Piperazine & Piperidine Derivatives, Chemical Abstracts, Jan. 30, 1978, 88(5):50920n.
Vippagunta, Acv. Drug Del. Rev., 2001, 48:3-26.
Walsh et al., Sexual dysfunction in the older women: An overview of the current understanding and management, Drugs Aging, 2004, 21(10):655-675.
Welsh, et al., Effect of Lactacidosis on Pyridine Nucleotide Stability During Ischemia in Mouse Brain, J Neurochemistry, 1987, 49(3):846-851.
Zajecka et al., Sexual function and satisfaction in the treatment of chronic major depression with nefazodone, psychotherapy, and their combination, J Psychiatry, Aug. 2002, 63(8):709-716.
Zverina, et al., The occurrence of atypical sexual experience among various female groups, Arch Sex Behav, 1987, 16(4):321-6.
Office Action in commonly owned Korean Patent Application No. 10-2008-7013699; dated Jun. 12, 2013, 10 pages.
Office Action in commonly owned Brazilian Patent Application No. PI0211601-4; dated Sep. 20, 2012 9 pages.
Gao et al., "Efficacy and Safety of Flibanserin in Women with Hypoactive Sexual Desire Disorder: A Systematic Review and Meta-Analysis", J Sex Med, 2015, vol. 12, pp. 2095-2104.
Robinson, et al., "First Pharmacological Therapy for Hypoactive Sexual Desire Disorder in Premenopausal Women: Flibanserin", Annals of Pharmacotherapy, 2016, vol. 50(2), pp. 125-132.
Jaspers et al., "Efficacy and Safety of Flibanserin for the Treatment of Hypoactive Sexual Desire Disorder in Women: A Systematic Review and Meta-analysis", Abstract downloaded at http://www.ncbi.nlm.nih.gov/pubmed/26927498 on May 19, 2016, pp. 1-2.
Taavoni et al.; Psychogeratrics; Hormone Replacement Therapy: Post-Menopausal Sex Life and Attitudes Towards Sex, 2005; 5:9-14, 6 pages.
Selective Serotonin Reuptake Inhibitors (SSRIs) Information; http://www.fda.gov/Drugs/DrugSafety/InformationbyDrugClass/ucm283587.htm as downloaded on Feb. 16, 2016; 2 pages.
Kurtel et al.; Journal of the American Society of Hypertension, Impaired Vasomotor Function Inducced by the Combination of Hypertension and Hypercholesterolemia, 2013; 7(1) pp. 14-23,10 pages.
Menopause Practice: A Clinician's Guide 3rd edition (NAMS 2007), 7 pages.
Katz et al.; Journal of Sex and Marital Therapy, The Relationship between Worry, Sexual Aversion, and Low Sexual Desire, 1999, vol. 25, Issue 4, abstract, 9 pages.
Office Action in European Patent Office in EP 09709701.8 dated Oct. 22, 2015.
Kibbe et al.; Hydroxypropyl Methlcellulose: Handbook of Pharmaceutical Excipients, 2000, 6 pages, XP-002376679.
Office Action in counterpart European Patent Application No. 09774901.4; dated Aug. 9, 2013, 4 pages.
Office Action in counterpart European Patent Application No. 07728833.0; dated Aug. 21, 2012, 5 pages.
Office Action in counterpart European Patent Application No. 06764270.2; dated Mar. 6, 2012, 4 pages.
Office Action in counterpart Australian Patent Application No. 2006311038; dated Aug. 25, 2011, 2pages.
Office Action in counterpart Australian Patent Application No. 2007247094; dated Aug. 30, 2011, 2 pages.
Office action in counterpart Brazilian Patent Application No. PI0311189-0; dated Jun. 26, 2012, 10 pages.
Office Action in counterpart European Patent Application No. 07787338.8; dated Jul. 6, 2012, 4 pages.
Office Action in commonly owned Brazilian Patent Application No. PI0213358-0; dated Jul. 24, 2015, 4 pages.
Sexual and Gender Identity Disorders, Diagnostic and Statistical Manual of Mental Disorders, Fourth Edition Text Revision, American Psychiatric Association, 2000, 34 pages, 535-566.
Katz et al.; Efficacy of Flibanserin in Women with Hypoactive Sexual Desire Disorder: Results from the BEGONIA Trial; J Sex Med 2013, 10, 9 pp. 1807-1815.
International Search Report for PCT/EP07/58301 dated Jul. 24, 2008.
International Search Report for PCT/EP07/58302 dated Jun. 4, 2008.
International Search Report for PCT/EP08/53592 dated Jun. 4, 2009.
Office Action in counterpart Canadian Patent Application No. 2,563,743; dated Apr. 3, 2013, 2 pages.
Thrombolytic Therapy: MedlinePlus Medical Encylopedia, http://www.nim.nih.gov/medlineplus/ency/article/007089.htm, accessed Sep. 17, 2015, pp. 1-5.
International Search Report for PCT/EP06/64825 dated Nov. 17, 2006.
International Search Report for PCT/EP07/57064 dated Nov. 6, 2007.
International Search Report for PCT/IB04/02286 dated Sep. 24, 2004.
International Search Report for PCT/EP05/04086 dated Oct. 11, 2005.
Office Action in commonly owned Brazilian Patent Application No. 122012029907-3; dated Mar. 24, 2015, 11 pages.
Elger et al., Oedema reduction by levemopamil in focal cerebral ischemia of spontaneously hypertensive rats studied by magnetic resonance imaging, 1994, European Journal of Pharmacology, vol. 254, pp. 65-71.
International Search Report for PCT/EP05/04081 dated Oct. 11, 2005.
Office Action in counterpart Canadian Patent Application No. 2,617,546; dated Mar. 25, 2013, 2 pages.
International Search Report for PCT/EP03/05226 dated Sep. 17, 2003.
Office Action in counterpart Canadian Patent Application No. 2,626,134; dated Aug. 24, 2012, 2 pages.
Office Action in counterpart Canadian Patent Application No. 2,626,797; dated Aug. 21, 2012, 3 pages.
Poster, presented Nov. 6, 2009 at Sexual Medicine Society of North American 2009 Fall Scientific Meeting, 3 pages.
Transcript of Poster, presented Nov. 6, 2009 at Sexual Medicine Society of North American 2009 Fall Scientific Meeting, "Pooled Clinical Trial Analysis of Flibanserin Safety and Tolerability in Premenopausal Women with Hypoactive Sexual Desire Disorder", 7 pages.

(56) References Cited

OTHER PUBLICATIONS

Office Action in commonly owned Canadian Patent Application No. 2,649,938; dated Jan. 10, 2014, 3 pages.
Office Action in commonly owned Canadian Patent Application No. 2,654,798; dated Jan. 23, 2014, 2 pages.
Office Action in commonly owned Canadian Patent Application No. 2,617,546; dated Jul. 26, 2012, 2 pages.
International Search Report for PCT/EP03/02184 dated Aug. 12, 2003.
Office Action in commonly owned Japanese Patent Application No. 2005-530787; dated Jun. 30, 2014, 2 pages.
Office Action in commonly owned European Patent Application No. 07728833.0; dated Apr. 9, 2013, 1 page.
Office Action in commonly owned Korean Patent Application No. 10-2008-7013699; dated Mar. 21, 2014, 5 pages.
Office Action in commonly owned Brazilian Patent Application No. PI0211601-4; dated Feb. 27, 2012 8 pages.
Office Action in commonly owned Chinese Patent Application No. 201310074677.5; dated Dec. 5, 2014, 8 pages.
Office Action in commonly owned European Patent Application No. 06807537.3; dated Mar. 8, 2013, 3 pages.
Office Action in commonly owned Canadian Patent Application No. 2,649,938; dated May 7, 2013, 3 pages.
Office Action in commonly owned Canadian Patent Application No. 2,654,798; dated May 7, 2013, 2 pages.
Office Action in commonly owned Canadian Patent Application No. 2,672,957; dated Nov. 1, 2013, 2 pages.
Office Action in counterpart Canadian Patent Application No. 2,563,743; dated Aug. 8, 2012, 2 pages.
Office Action in commonly owned Canadian Patent Application No. 2,802,600; dated Nov. 28, 2013, 2 pages.
Office Action in commonly owned Canadian Patent Application No. 2,682,015; dated Aug. 26, 2014, 2 pages.
Office Action in commonly owned Canadian Patent Application No. 2,802,600; dated Sep. 25, 2014, 2 pages.
International Search Report for PCT/EP02/11103 dated Jan. 14, 2003.
Office Action in commonly owned Korean Patent Application No. 10-2013-7033147; dated Feb. 28, 2014, 7 pages.
Office Action in commonly owned Chinese Patent Application No. 201310074677.5; dated Mar. 24, 2014, 8 pages.
Dennerstein et al.; Hypoactive Sexual Desire Disorder in Menopausal Women: A Survey of Western European Women; Journal of Sexual Medicine 2006; No. 3, 11 pages.
Leiblum et al.; Hypoactive Sexual Desire Disorder in Postmenopausal Women: US Results from the Women's International Study of Health and Sexuality (WISHeS); Menopause: The Journal of the North American Menopause Society 2006; vol. 13, No. 1, 11 pages.
Simon et al.; Efficacy and Safety of Flibanserin in Postmenopausal Women with Hypoactive Sexual Desire Disorder Results of the SNOWDROP Trial; Menopause: The Journal of the North American Menopause Society 2013; vol. 21, No. 6, 8 pages.
Office Action in commonly owned Canadian Patent Application No. 2,699,414; dated Oct. 30, 2014, 3 pages.
Crenshaw; The Sexual Aversion Syndrome; J. Sex Marital Ther.; 1985, vol. 11, Issue 4, abstract; 1 page.
Muir et al.; Dose Optimization of Intravenous Magnesium Sulfate After Acute Stroke; Stroke; May 1996; 29:918-923; 7 pages.
Khaled; Role of 5-HT Receptors in Treatment of Overactive Bladder; Drugs Today (Barc), Aug. 2003; 39 (8); 599-607 (abstract only); 2 pages.
International Search Report for PCT/EP02/08466 dated Nov. 21, 2002.
Nitti; Duloxetine: A New Pharmacologic Therapy for Stress Urinary Incontinence; Reviews in Urology; 2004; vol. 6 (Suppl. 3): S46-S55; 8 pages.
Rezakhaniha; Efficacy of Desmopressin in Treatment of Nocturia in Elderly Men; J Res Med Sci.; Apr. 2011; 16 (4): 516-523; 8 pages.
Mayo Clinic: Overactive Bladder, 2015; http://www.mayoclinic.org/diseases-conditions/overactive-bladder/basics/prevention/con-2; 3 pages.
Urinary Incontinence—Prevention—NHS Choices, 2014, http://www.nhs.uk/Conditions/Incontinence-urinary/Pages/Prevention.aspx.
Borsini et al.; Flibanserin: Antidepressant, 5HT(1A) Receptor Agonist 5-HT2 Receptor Antagonist: Drugs of the Future; (1998) vol. 23, No. 1; pp. 9-16; 6 pages.
Dow; Using Dow Excipients for Controlled Release of Drugs in Hydrophilic Matrix Systems, 2006; pp. 1-34,36 pages.
International Search Report for PCT/US05/24623 dated Nov. 4, 2005.
International Search Report for PCT/EP00/08891 dated Jan. 30, 2001.
Office Action in commonly owned Canadian Patent Application No. 2,682,015; dated Dec. 20, 2013, 3 pages.
International Search Report for PCT/US00/18217 dated Oct. 26, 2000.

FLIBANSERIN FOR THE TREATMENT OF URINARY INCONTINENCE AND RELATED DISEASES

The invention relates to the use of Flibanserin for the treatment or prevention of urinary incontinence and related diseases. In a further embodiment, the instant invention is directed to pharmaceutical combinations comprising flibanserin as one active ingredient in combination with at least one additional active ingredient for the treatment or prevention of urinary incontinence and related diseases.

DESCRIPTION OF THE INVENTION

The compound 1-[2-(4-(3-trifluoromethyl-phenyl)piperazin-1-yl)ethyl]-2,3-dihydro-1H-benzimidazol-2-one (flibanserin) is disclosed in form of its hydrochloride in European Patent Application EP-A-526434 and has the following chemical structure:

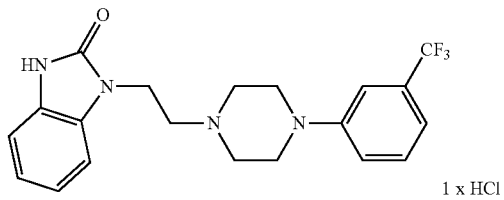 [SMILES: O=c1[nH]c2ccccc2n1CCN1CCN(c2cccc(C(F)(F)F)c2)CC1]

1 x HCl

Flibanserin shows affinity for the 5-HT1A and 5-HT2-receptor. It is therefore a promising therapeutic agent for the treatment or prevention of a variety of diseases, for instance depression, schizophrenia, and anxiety.

Now, experiments provided evidence, that flibanserin can not only be used for the aforementioned diseases but also for the treatment or prevention of urinary incontinence.

In one embodiment the present invention relates to the use of a therapeutically effective amount of Flibanserin 1, optionally in form the free base, the pharmacologically acceptable acid addition salts and/or optionally in form of the hydrates and/or solvates thereof for the manufacture of a medicament for the treatment or prevention of urinary incontinence.

With regard to the present invention the term "urinary incontinence" includes stress urinary incontinence, urge urinary incontinence, urgency, mixed urinary incontinence and overactive bladder syndrome.

Urinary Incontinence (UI), as other Lower Urinary Tract Dysfunctions, can be described as a symptom, as a sign, as an urodynamic observation or as a condition as a whole. The symptom of UI is defined as "the complaint of any involuntary leakage of urine" (Abrams P, Cardozo Neurourol Urodyn 2002; 21:167-178).

Stress urinary Incontinence (SUI) is defined as the complaint of involuntary leakage on effort or exertion, or on sneezing or coughing. It occurs because a positive urethral pressure gradient over bladder pressure cannot be maintained during abrupt increases in abdominal pressure. This insufficient urethral closure pressure can be the consequence of anatomical defects in the pelvic floor muscles leading to urethral hypermobility, intrinsic deficiency of the external urethral sphincter or a combination of both.

SUI is more prevalent in women than in men. In women pregnancy, childbirth and parity are the most important inciting factors. In men SUI is infrequent and mainly referred as a sequale after prostate surgery (Transurethral Prostate Resection for Benign Prostate Hyperplasia or Radical Prostatectomy for Prostate Cancer). Stress Urinary Incontinence is the most common type of UI in women, with 78% of women presenting with the symptom of SUI in either pure (49%) or mixed (29%) forms.

Urge urinary Incontinence (UUI) is defined as the complaint of involuntary leakage accompanied by or immediately preceded by urgency. Urgency is the complaint of a sudden compelling desire to pass urine, which may be difficult to defer.

Urge urinary incontinence is one of the symptoms which is categorised under the syndrome of Overactive Bladder (OAB). According to the ICS definition, OAB is characterised by an irresistible imperative need to urinate, which may or may not be associated with urge urinary incontinence, usually with increased frequency of micturition and nocturnal urination. Pathophysiologically, this complaint may be based on involuntary detrusor contractions during the filling phase, the cause of which may be neurogenic or non-neurogenic (idiopathic) by nature. Urgency and urge urinary incontinence are extremely unpleasant and troublesome to those affected, leading to considerable impairment of their quality of life and psychological, professional, domestic, physical and sexual problems.

Mixed urinary incontinence is defined as the complaint of involuntary leakage associated with urgency and also with exertion, effort, sneezing or coughing. Again more women are affected than men.

In another embodiment the present invention relates to the use of a therapeutically effective amount of Flibanserin 1, optionally in form the free base, the pharmacologically acceptable acid addition salts and/or optionally in form of the hydrates and/or solvates thereof for the manufacture of a medicament for the treatment or prevention of overactive bladder syndrome.

In another embodiment the present invention relates to the use of a therapeutically effective amount of Flibanserin 1, optionally in form the free base, the pharmacologically acceptable acid addition salts and/or optionally in form of the hydrates and/or solvates thereof for the manufacture of a medicament for the treatment or prevention of urge urinary incontinence.

In another embodiment the present invention relates to the use of a therapeutically effective amount of Flibanserin 1, optionally in form the free base, the pharmacologically acceptable acid addition salts and/or optionally in form of the hydrates and/or solvates thereof for the manufacture of a medicament for the treatment or prevention of urgency.

In another embodiment the present invention relates to the use of a therapeutically effective amount of Flibanserin 1, optionally in form the free base, the pharmacologically acceptable acid addition salts and/or optionally in form of the hydrates and/or solvates thereof for the manufacture of a medicament for the treatment or prevention of stress urinary incontinence.

In another embodiment the present invention relates to the use of a therapeutically effective amount of Flibanserin 1, optionally in form the free base, the pharmacologically acceptable acid addition salts and/or optionally in form of the hydrates and/or solvates thereof for the manufacture of a medicament for the treatment or prevention of mixed urinary incontinence.

Another embodiment of the present invention relates to methods of treating or preventing of any of the aforementioned disorders, comprising the administration of a therapeutically effective amount of Flibanserin 1, optionally in form the free base, the pharmacologically acceptable acid addition salts and/or optionally in form of the hydrates and/or solvates thereof.

As Flibanserin 1 can not only be used as a monotherapy but also in combination with other active ingredients useful for treatment of urinary incontinence, another embodiment of the invention relates to new pharmaceutical compositions comprising a therapeutically effective amount of Flibanserin 1, optionally in form the free base, the pharmacologically acceptable acid addition salts and/or optionally in form of the hydrates and/or solvates thereof, as one active ingredient in combination with a therapeutically effective amount one or more, preferably one active ingredient 2 useful for treatment of urinary incontinence.

The compositions according to the invention may contain Flibanserin 1 and the one or more additional active ingredient 2 in a single formulation or in separate formulations (multiple dosage form). If Flibanserin 1 and the one or more, preferably one active ingredient 2 are present in separate formulations these separate formulations may be administered simultaneously or sequentially.

In a further embodiment, the present invention is directed to pharmaceutical compositions comprising a therapeutically effective amount of Flibanserin 1, optionally in form the free base, the pharmacologically acceptable acid addition salts and/or optionally in form of the hydrates and/or solvates thereof, as one active ingredient in combination with a therapeutically effective amount of one or more, preferably one active ingredient 2 useful for treatment of urinary incontinence, wherein 2 is selected from the group consisting of antimuscarinic agents 2a, vasopressin agonists 2b, Serotonin/Noradrenaline modulators 2c and β3 agonists 2d.

In a further embodiment, the present invention is directed to pharmaceutical compositions comprising a therapeutically effective amount of Flibanserin 1, optionally in form the free base, the pharmacologically acceptable acid addition salts and/or optionally in form of the hydrates and/or solvates thereof, as one active ingredient in combination with a therapeutically effective amount of one or more, preferably one antimuscarinic agent 2a, optionally in form of the pharmaceutically acceptable salts, in form of the hydrates and/or solvates and optionally in the form of the individual optical isomers, mixtures of the individual enantiomers or racemates thereof and optionally in combination with a pharmaceutical acceptable excipient. Preferred antimuscarinic agents 2a include Tolterodine, Oxybutynin, Darifenacin, Propiverine, Solifenacin and Trospium.

In a further embodiment, the present invention is directed to pharmaceutical compositions comprising a therapeutically effective amount of Flibanserin 1, optionally in form the free base, the pharmacologically acceptable acid addition salts and/or optionally in form of the hydrates and/or solvates thereof, as one active ingredient in combination with a therapeutically effective amount of one or more, preferably one vasopressin agonist 2b, optionally in form of the pharmaceutically acceptable salts, in form of the hydrates and/or solvates and optionally in the form of the individual optical isomers, mixtures of the individual enantiomers or racemates thereof and optionally in combination with a pharmaceutical acceptable excipient. A preferred vasopressin agonist 2b is Desmopressin.

In a further embodiment, the present invention is directed to pharmaceutical compositions comprising a therapeutically effective amount of Flibanserin 1, optionally in form the free base, the pharmacologically acceptable acid addition salts and/or optionally in form of the hydrates and/or solvates thereof, as one active ingredient in combination with a therapeutically effective amount of one or more, preferably one Serotonin/Noradrenaline modulator 2c, optionally in form of the pharmaceutically acceptable salts, in form of the hydrates and/or solvates and optionally in the form of the individual optical isomers, mixtures of the individual enantiomers or racemates thereof and optionally in combination with a pharmaceutical acceptable excipient. Preferred Serotonin/Noradrenaline modulators 2c include Venlafaxine, Duloxetine, Reboxetine and Cizoliritine.

In a further embodiment, the present invention is directed to pharmaceutical compositions comprising a therapeutically effective amount of Flibanserin 1, optionally in form the free base, the pharmacologically acceptable acid addition salts and/or optionally in form of the hydrates and/or solvates thereof, as one active ingredient in combination with a therapeutically effective amount of one or more, preferably one β3 agonist 2d, optionally in form of the pharmaceutically acceptable salts, in form of the hydrates and/or solvates and optionally in the form of the individual optical isomers, mixtures of the individual enantiomers or racemates thereof and optionally in combination with a pharmaceutical acceptable excipient. Preferred β3 agonists include AD9677/TAK677, CL 316,243, SB 418790, L-796568, BMS-196085, BRL-35135A, CGP12177A, BTA-243, GW 427353, Trecanidine, Zeneca D7114, SR 59119, solabegron, CL616243, 2-[4-(2-[[(1S,2R)-2-hydroxy-2-(4-hydroxyphenyl)-1-methylethyl]amino]ethyl)phenoxy]-2-methylpropionic acid, BRL37344A and CGP-12177A Flibanserin 1 can optionally be used in form of its pharmaceutically acceptable acid addition salts. Suitable acid addition salts include for example those of the acids selected from, succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularly the hydrochloride, are preferred. If flibanserin is used in form of the free base, it is preferably used in form of flibanserin polymorph A as disclosed in WO 03/014079.

The active ingredients 2 which are suitable to be combined with 1 within the teaching of the instant invention and which are mentioned hereinbefore may also be capable of forming acid addition salts with pharmaceutically acceptable acids. Representative salts include the following: Acetate, Benzenesulfonate, Benzoate, Bicarbonate, Bisulfate, Bitartrate. Borate, Bromide, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methyglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

Furthermore, where the compounds 2 carry an acidic moiety, suitable pharmaceutically acceptable salts thereof may include alkali metal salts, e.g., sodium or potassium salts; alkaline earth metal salts, e. g., calcium or magnesium salts; and salts formed with suitable organic ligands. e.g., quaternary ammonium salts.

The compounds 2 may have chiral centers and occur as racemates, racemic mixtures and as individual diastereomers or enantiomers with all isomeric forms being included in the present invention. Therefore, where a compound is chiral, the separate enantiomers, substantially free of the other, are included within the scope of the invention. Further included are all mixtures of the two enantiomers. Also included within the scope of the invention are polymorphs and hydrates of the compounds of the instant invention.

The present invention includes within its scope prodrugs of the compounds 1 and 2. In general, such prodrugs will be functional derivatives of the compounds of this invention which are readily convertible in vivo into the required compound.

The term "therapeutically effective amount" shall mean that amount of a drug or pharmaceutical agent that will elicit the biological or medical response of a tissue, system, animal or human that is being sought by a researcher or clinician.

As used herein, the term "composition" is intended to encompass a product comprising the specified ingredients in the specified amounts, as well as any product which results, directly or indirectly, from combination of the specified ingredients in the specified amounts.

According to the present invention Flibanserin 1 may be administered as a monotherapy or together with component 2 as a combination therapy. If Flibanserin 1 is administered in combination with component 2, 1 and 2 may be administered separately or together in one pharmaceutical composition. In addition, the administration of one element of the combination of the present invention may be prior to, concurrent to, or subsequent to the administration of the other element of the combination.

Flibanserin 1 or the elements of the combination of 1 and 2 may be administered by oral, parenteral (e.g., Intramuscular, intraperitoneal. Intravenous or subcutaneous injection, or implant), buccal, nasal, vaginal, rectal, sublingual, or topical (e.g. ocular eyedrop) routes of administration and may be formulated, alone or together, in suitable dosage unit formulations containing conventional non-toxic pharmaceutically acceptable carriers, adjuvants and vehicles appropriate for each route of administration.

The pharmaceutical compositions, dosage forms, kit of parts for the administration of 1 or 1 and 2 of this invention may conveniently be presented in dosage unit form and may be prepared by any of the methods well known in the art of pharmacy. All methods include the step of bringing the active ingredient into association with the carrier which is constituted of one or more accessory ingredients. In general, the pharmaceutical compositions, dosage forms, kit of parts are prepared by uniformly and intimately bringing the active ingredients into association with a liquid carrier or a finely divided solid carrier or both, and then, if necessary, shaping the product into the desired dosage form. In the pharmaceutical compositions the active compounds are included in an amount sufficient to produce the desired pharmacologic effect.

The pharmaceutical formulations, compositions, dosage forms or kit of parts containing 1 and/or 1, separately or together, that are suitable for oral administration may be in the form of discrete units such as hard or soft capsules, tablets, troches or lozenges, each containing a predetermined amount of the active ingredients; in the form of a dispersible powder or granules; in the form of a solution or a suspension in an aqueous liquid or non-aqueous liquid; in the form of syrups or elixirs; or in the form of an oil-in-water emulsion or a water-in-oil emulsion.

Dosage forms intended for oral use may be prepared according to any method known to the art for the manufacture of pharmaceutical formulations and such compositions.

The excipients used may be for example, (a) inert diluents such as mannitol, sorbitol, calcium carbonate, pregelatinized starch, lactose, calcium phosphate or sodium phosphate; (b) granulating and disintegrating agents, such as povidone, copovidone, hydroxypropylmethylcellulose, corn starch, alginic acid, crospovidone, sodiumstarchglycolate, croscarmellose, or polacrilin potassium; (c) binding agents such as microcrystalline cellulose or acacia; and (d) lubricating agents such as magnesium stearate, stearic acid, fumaric acid or talc.

In some cases, formulations for oral use may be in the form of hardgelatin or HPMC capsules wherein the active ingredients 1 and/or 2, separately or together, are mixed with an inert solid diluent, for example pregelatinized starch, calcium carbonate, calcium phosphate or kaolin, or dispensed via a pellet formulation. They may also be in the form of soft gelatin capsules wherein the active ingredient is mixed with water or an oil medium, for example peanut oil, liquid paraffin, medium chain triglycerides or olive oil.

The tablets, capsules or pellets may be uncoated or they may be coated by known techniques to delay disintegration and absorption in the gastrointestinal tract and thereby provide a delayed action or sustained action over a longer period. For example, a time delay material such as celluloseacetate phtalate or hydroxypropylcellulose acetate succinate or sustained release material such as ethylcellulose or ammoniomethacrylate copolymer (type B) may be employed.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, perfuming and preserving agents.

Aqueous suspensions normally contain the active materials 1 and/or 2, separately or together, in admixture with excipients suitable for the manufacture of aqueous suspensions. Such excipients may be (a) suspending agents such as hydroxy ethylcellulose, sodium carboxymethylcellulose, methylcellulose, hydroxypropylmethylcellulose, sodium alginate, polyvinylpyrrolidone, gum tragacanth and gum acacia; (b) dispersing or wetting agents which may be (b.1) a naturally-occurring phosphatide such as lecithin, (b.2) a condensation product of an alkylene oxide with a fatty acid, for example, polyoxyethylene stearate, (b.3) a condensation product of ethylene oxide with a long chain aliphatic alcohol, for example heptadecaethyleneoxycetanol, (b.4) a condensation product of ethylene oxide with a partial ester derived from a fatty acid and a hexitol such as polyoxyethylene sorbitol monooleate, or (b.5) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents, such as sucrose or saccharin.

Oily suspensions may be formulated by suspending the active ingredients 1 and/or 2, separately or together, in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the active ingredient 1 and/or 2, separately or together in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical formulations, compositions, dosage forms or kit of parts of the invention may also be in the form of oil-in-water emulsions. The oily phase may be a vegetable oil such as olive oil or *arachis* oils, or a mineral oil such as liquid paraffin or a mixture thereof.

Suitable emulsifying agents may be (a) naturally-occurring gums such as gum acacia and gum tragacanth, (b) naturally-occurring phosphatides such as soybean and lecithin, (c) esters or partial esters derived from fatty acids and hexitol anhydrides, for example, sorbitan monooleate, (d) condensation products of said partial esters with ethylene oxide, for example polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a preservative and flavoring and coloring agents.

The pharmaceutical formulations, compositions, dosage forms or kit of parts containing 1 and/or 2, separately or together may be in the form of a sterile injectable aqueous or oleagenous suspension or solution. The suspension may be formulated according to known methods using those suitable dispersing or wetting agents and suspending agents which have been mentioned above. The sterile injectable preparation may also be a sterile injectable solution or suspension in a non toxic parenterally-acceptable diluent or solvent, for example as a solution in 1,3-butane-diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Preparations according to this invention containing J and/or 1 and /or 2, separately or together, for parenteral administration include sterile aqueous or non-aqueous solutions, suspension, or emulsions.

Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be reconstituted in sterile water, or some other sterile injectable medium immediately before use. The combination of this invention may also be administered in the form of suppositories for rectal administration. This composition can be prepared by mixing the drugs with a suitable non-irritating excipient which is solid at ordinary temperatures but liquid at the rectal temperature and will therefore melt in the rectum to release the drug. Such materials are cocoa butter, hard fat, and polyethylene glycols. Compositions for buccal, nasal or sublingual administration are also prepared with standard excipients well known in the art.

For topical administration the formulations, compositions, dosage forms or kit of parts of this invention containing 1 and/or 2, separately or together may be formulated in liquid or semi-liquid preparations such as liniments, lotions, applications; oil-in-water or water-in-oil emulsions such as creams, ointments, jellies or pastes, including tooth-pastes; or solutions or suspensions such as drops, and the like.

The dosage of the active ingredients in the compositions of this invention may be varied. However, it is necessary that the amount of Flibanserin 1 for the administration as a monotherapy or the active ingredients 1 and 2, for the administration as a combination therapy, be such that a suitable dosage form is obtained. The selected dosage and the dosage form depend upon the desired therapeutic effect, on the route of administration and on the duration of the treatment. Dosage ranges in the combination are approximately one tenth to one times the clinically effective ranges required to induce the desired therapeutic effect, respectively when the compounds are used singly.

The beneficial effects of Flibanserin 1, optionally in form the free base, the pharmacologically acceptable acid addition salts and/or optionally in form of the hydrates and/or solvates thereof, can be observed regardless of whether the disturbance existed lifelong or was acquired, and independent of etiologic origin (organic—both, physically and drug induced-, psychogen, a combination of organic—both, physically and drug induced-, and psychogen, or unknown).

Within the instant invention Flibanserin 1 is preferably administered in such an amount that per single dosage between 5 to 200 mg of Flibanserin 1 are applied. Preferred are ranges of between 10 to 150 mg, particular preferred 20 to 100 mg of Flibanserin 1. Suitable dosage forms may contain for instance 20, 25, 30, 35, 40, 45, 50, 55, 60, 65, 70, 75, 80, 85, 90, 95 or 100 mg of Flibanserin 1. The aforementioned values are based on Flibanserin 1 in form of the free base. If Flibanserin 1 is applied in form of one of its acid addition salts, the corresponding values are readily calculable from the aforementioned values.

Within the instant invention the antimuscarinic agents 2a are preferably administered in such an amount that per day between 0.01 to 200 mg are applied. Preferred are ranges of between 0.5 to 100 mg, particular preferred 1 to 50 mg of the antimuscarinic agents 2a. Suitable dosage forms may contain for instance 0.01, 0.05, 0.5, 1, 2, 5, 10, 20, 25, 50, 100 or 200 mg of the antimuscarinic agents 2a. Advantageously, the compounds 2a of the present invention may be administered in a single daily dose, or the total daily dosage may be administered in divided doses of two, three or four times daily.

Within the instant invention the vasopressin agonist 2b are preferably administered in such an amount that per day between 0.01 to 100 mg are applied. Preferred are ranges of between 0.5 to 100 mg, particular preferred 1 to 50 mg of the vasopressin agonist 2b. Suitable dosage forms may contain for instance 0.01, 0.05, 0.5, 1, 2, 5, 10, 20, 25, 50 or 100 mg of the vasopressin agonist 2b. Advantageously, the compounds 2b of the present invention may be administered in a single daily dose, or the total daily dosage may be administered in divided doses of two, three or four times daily.

Within the instant invention the Serotonin/Noradrenaline modulators 2c are preferably administered in such an amount that per day between 0.1 to 200 mg are applied. Preferred are ranges of between 0.5 to 150 mg, particular preferred 1 to 100 mg of the Serotonin/Noradrenaline modulators 2c. Suitable dosage forms may contain for instance 0.1, 0.5, 1, 2, 5, 10, 20, 25, 50, 100 or 200 mg of the Serotonin/Noradrenaline modulators 2c. Advantageously, the compounds 2c of the present invention may be administered in a single daily dose, or the total daily dosage may be administered in divided doses of two, three or four times daily.

Within the instant invention the $\beta 3$ agonists 2d are preferably administered in such an amount that per day between 0.01 to 1000 mg are applied. Preferred are ranges of between 0.1 to 500 mg, particular preferred 1 to 200 mg of the $\beta 3$ agonists 2d. Suitable dosage forms may contain for instance 0.1, 0.5, 1, 2, 5, 10, 20, 25, 50, 100 or 200 mg of the $\beta 3$ agonists. Advantageously, the compounds 2d of the present invention may be administered in a single daily dose, or the total daily dosage may be administered in divided doses of two, three or four times daily.

In another embodiment the invention relates to a method for the treatment or prevention of urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one active ingredient 2, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

In another embodiment the invention relates to a method for the treatment or prevention of overactive bladder syndrome, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one active ingredient 2, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

In another embodiment the invention relates to a method for the treatment or prevention of urge urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one active ingredient 2, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

In another embodiment the invention relates to a method for the treatment or prevention of urgency, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one active ingredient 2, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

In another embodiment the invention relates to a method for the treatment or prevention of stress urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one active ingredient 2, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

In another embodiment the invention relates to a method for the treatment or prevention of mixed urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one active ingredient 2, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one active ingredient 2, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of any of the aforementioned disorders.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of any of the aforementioned disorders in combination with one or more, preferably one active ingredient 2 optionally in form of the pharmaceutically acceptable salts, in form of the hydrates and/or solvates and optionally in the form of the individual optical isomers, mixtures of the individual enantiomers or racemates thereof.

In another embodiment the invention relates to a method for the treatment or prevention of one of the aforementioned diseases selected from the group consisting of urinary incontinence, overactive bladder syndrome, urge urinary incontinence, urgency, stress urinary incontinence and mixed urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one antimuscarinic agents 2a, optionally in form of the pharmaceutically acceptable salts, in form of the hydrates and/or solvates and optionally in the form of the individual optical isomers, mixtures of the individual enantiomers or racemates thereof, separately or together within one pharmaceutical composition. Preferred antimuscarinic agents 2a include Tolterodine, Oxybutynin, Darifenacin, Propiverine, Solifenacin and Trospium.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one antimuscarinic agent 2a, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of any of the aforementioned disorders. Preferred antimuscarinic agents 2a include Tolterodine, Oxybutynin, Darifenacin, Propiverine, Solifenacin and Trospium. Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of any of the aforementioned disorders in combination with one or more, preferably one antimuscarinic agent 2a, optionally in form of the pharmaceutically acceptable salts, in form of the hydrates and/or solvates and optionally in the form of the individual optical isomers, mixtures of the individual enantiomers or racemates thereof. Preferred antimuscarinic agents 2a include Tolterodine, Oxybutynin, Darifenacin, Propiverine, Solifenacin and Trospium.

In another embodiment the invention relates to a method for the treatment or prevention of one of the aforementioned diseases selected from the group consisting of urinary incontinence, overactive bladder syndrome, urge urinary incontinence, urgency, stress urinary incontinence and mixed urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one vasopressin agonist 2b, optionally in form of the pharmaceutically acceptable salts, in form of the hydrates and/or solvates and optionally in the form of the individual optical isomers, mixtures of the individual enantiomers or racemates thereof, separately or together within one pharmaceutical composition. A preferred vasopressin agonist 2b is Desmopressin.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one vasopressin agonist 2b, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of any of the aforementioned disorders. A preferred vasopressin agonist 2b is Desmopressin.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of any of the aforementioned disorders in combination with one or more, preferably one vasopressin agonist 2b, optionally in form of the pharmaceutically acceptable salts, in form of the hydrates and/or solvates and optionally in the form of the individual optical isomers, mixtures of the individual enantiomers or racemates thereof. A preferred vasopressin agonist 2b is Desmopressin.

In another embodiment the invention relates to a method for the treatment or prevention of one of the aforementioned diseases selected from the group consisting of urinary incontinence, overactive bladder syndrome, urge urinary incontinence, urgency, stress urinary incontinence and mixed urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one Serotonin/Noradrenaline modulator 2c, optionally in form of the pharmaceutically acceptable salts, in form of the hydrates and/or solvates and optionally in the form of the individual optical isomers, mixtures of the individual enantiomers or racemates thereof, separately or together within one pharmaceutical composition. Preferred Serotonin/Noradrenaline modulators 2c include Venlafaxine, Duloxetine, Reboxetine and Cizoliritine.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one Serotonin/Noradrenaline modulator 2c, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of any of the aforementioned disorders. Preferred Serotonin/Noradrenaline modulators 2c include Venlafaxine, Duloxetine, Reboxetine and Cizoliritine.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of any of the aforementioned disorders in combination with one or more, preferably one Serotonin/Noradrenaline modulator 2c, optionally in form of the pharmaceutically acceptable salts, in form of the hydrates and/or solvates and optionally in the form of the individual optical isomers, mixtures of the individual enantiomers or racemates thereof. Preferred Serotonin/Nor-adrenaline modulators 2c include Venlafaxine, Duloxetine, Reboxetine and Cizoliritine.

In another embodiment the invention relates to a method for the treatment or prevention of one of the aforementioned diseases selected from the group consisting of urinary incontinence, overactive bladder syndrome, urge urinary incontinence, urgency, stress urinary incontinence and mixed urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one β3 agonist 2d, optionally in form of the pharmaceutically acceptable salts, in form of the hydrates and/or solvates and optionally in the form of the individual optical isomers, mixtures of the individual enantiomers or racemates thereof, separately or together within one pharmaceutical composition. Preferred β3 agonists 2d include AD9677/TAK677, CL 316,243, SB 418790, L-796568, BMS-196085, BRL-35135A, CGP12177A, BTA-243, GW 427353, Trecanidine, Zeneca D7114, SR 59119, solabegron, CL616243, 2-[4-(2-[[(1S,2R)-2-hydroxy-2-(4-hydroxyphenyl)-1-methylethyl] amino]ethyl)phenoxy]-2-methylpropionic acid, BRL37344A and CGP-12177A.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one β3 agonist 2d, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of any of the aforementioned disorders. Preferred β3 agonists 2d include AD9677/TAK677, CL 316,243, SB 418790, L-796568, BMS-196085, BRL-35135A, CGP12177A, BTA-243, GW 427353, Trecanidine, Zeneca D7114, SR 59119, solabegron, CL616243, 2-[4-(2-[[(1S,2R)-2-hydroxy-2-(4-hydroxyphenyl)-1-methylethyl]amino]ethyl) phenoxy]-2-methylpropionic acid, BRL37344A and CGP-12177A.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of any of the aforementioned disorders in combination with one or more, preferably one β3 agonist 2d, optionally in form of the pharmaceutically acceptable salts, in form of the hydrates and/or solvates and optionally in the form of the individual optical isomers, mixtures of the individual enantiomers or racemates thereof. Preferred β3 agonists 2d include AD9677/TAK677, CL 316,243, SB 418790, L-796568, BMS-196085, BRL-35135A. CGP12177A, BTA-243, GW 427353, Trecanidine, Zeneca D7114, SR 59119, solabegron, CL616243, 2-[4-(2-[[(1S,2R)-2-hydroxy-2-(4-hydroxyphenyl)-1-methylethyl]amino]ethyl)phenoxy]-2-methylproponic acid, BRL37344A and CGP-12177A.

In a preferred embodiment the invention relates to a method for the treatment or prevention of overactive bladder syndrome, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one antimuscarinic agents 2a, selected from the group consisting of Tolterodine, Oxybutynin, Darifenacin, Propiverine, Solifenacin and Trospium, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one antimuscarinic agent 2a, selected from the group consisting of Tolterodine, Oxybutynin, Darifenacin, Propiverine, Solifenacin and Trospium, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of the overactive bladder syndrome.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of overactive bladder syndrome in combination with one or more, preferably one antimuscarinic agent 2a, selected from the group consisting of Tolterodine, Oxybutynin, Darifenacin, Propiverine, Solifenacin and Trospium, optionally in form of the pharmaceutically acceptable salts, in form of the hydrates and/or solvates and optionally in the form of the individual optical isomers, mixtures of the individual enantiomers or racemates thereof.

In a preferred embodiment the invention relates to a method for the treatment or prevention of urge urinary incontinence, comprising the administration of a therapeutically effective amount of Flibanserin 1, optionally in form the free base, the pharmacologically acceptable acid addition salts and/or optionally in form of the hydrates and/or solvates thereof. In combination with a therapeutically effective amount of one or more, preferably one antimuscarinic agents 2a, selected from the group consisting of Tolterodine, Oxybutynin, Darifenacin, Propiverine, Solifenacin and Trospium, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one antimuscarinic agent 2a, selected from the group consisting of Tolterodine, Oxybutynin, Darifenacin, Propiverine, Solifenacin and Trospium, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of urge urinary incontinence.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of urge urinary incontinence in combination with one or more, preferably one antimuscarinic agent 2a, selected from the group consisting of Tolterodine, Oxybutynin, Darifenacin, Propiverine, Solifenacin and Trospium, optionally in form of the pharmaceutically acceptable salts, in form of the hydrates and/or solvates and optionally in the form of the individual optical isomers, mixtures of the individual enantiomers or racemates thereof.

In a preferred embodiment the invention relates to a method for the treatment or prevention of overactive bladder syndrome, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of the vasopressin agonist 2b Desmopressin, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

Another embodiment of the present invention relates to the use of the combinations of Flibanserin 1, optionally in form the free base, the pharmacologically acceptable acid addition salts and/or optionally in form of the hydrates and/or solvates thereof, and of the vasopressin agonist 2b Desmopressin, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of the overactive bladder syndrome.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of the overactive bladder syndrome in combination with the vasopressin agonist 2b Desmopressin, optionally in form of the pharmaceutically acceptable salts, in form of the hydrates and/or solvates and optionally in the form of the individual optical isomers, mixtures of the individual enantiomers or racemates thereof.

In a preferred embodiment the invention relates to a method for the treatment or prevention of urge urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of the vasopressin agonist 2b Desmopressin, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

Another embodiment of the present invention relates to the use of the combinations of Flibanserin 1, optionally in form the free base, the pharmacologically acceptable acid addition salts and/or optionally in form of the hydrates and/or solvates thereof, and of the vasopressin agonist 2b Desmopressin, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of urge urinary incontinence.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of urge urinary incontinence in combination with the vasopressin agonist 2b Desmopressin, optionally in form of the pharmaceutically acceptable salts, in form of the hydrates and/or solvates and optionally in the form of the individual optical isomers, mixtures of the individual enantiomers or racemates thereof.

In a preferred embodiment the invention relates to a method for the treatment or prevention of stress urinary incontinence, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one Serotonin/Noradrenaline modulator 2c, selected from the group consisting of Venlafaxine. Duloxetine, Reboxetine and Cizoliritine, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one Serotonin/Noradrenaline modulator 2c, selected from the group consisting of Venlafaxine, Duloxetine, Reboxetine and Cizolirtine, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of stress urinary incontinence.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of stress urinary incontinence in combination with of one or more, preferably one Serotonin/Noradrenaline modulator 2c, selected from the group consisting of Venlafaxine, Duloxetine, Reboxetine and Cizoliritine, optionally in form of the pharmaceutically acceptable salts, in form of the hydrates and/or solvates and optionally in the form of the individual optical isomers, mixtures of the individual enantiomers or racemates thereof.

In a preferred embodiment the invention relates to a method for the treatment or prevention of overactive bladder syndrome, comprising the administration of a therapeutically effective amount of Flibanserin 1, optionally in form the free base, the pharmacologically acceptable acid addition salts and/or optionally in form of the hydrates and/or solvates thereof, in combination with a therapeutically effective amount of one or more, preferably one β3 agonist 2d, selected from the group consisting of AD9677/TAK677, CL 316,243. SB 418790. L-796568, BMS-196085, BRL-35135A. CGP12177A, BTA-243. GW 427353. Trecanidine, Zeneca D7114. SR 59119, solabegron. CL616243, 2-[4-(2-[[(1S,2R)-2-hydroxy-2-(4-hydroxyphenyl)-1-methylethyl]amino]ethyl)phenoxy]-2-methylpropionic acid, BRL37344A and CGP-12177A, optionally in form of the pharmaceutically acceptable salts, in form of the hydrates and/or solvates and optionally in the form of the individual optical isomers, mixtures of the individual enantiomers or racemates thereof, separately or together within one pharmaceutical composition.

Another embodiment of the present invention relates to the use of the combinations of Flibanserin 1, optionally in form the free base, the pharmacologically acceptable acid addition salts and/or optionally in form of the hydrates and/or solvates thereof, and of one or more, preferably one β3 agonist 2d, selected from the group consisting of AD9677/TAK677, CL 316,243, SB 418790, L-796568, BMS-196085, BRL-35135A, CGP12177A, BTA-243, GW 427353, Trecanidine, Zeneca D7114, SR 59119, solabegron, CL616243, 2-[4-(2-[[(1S,2R)-2-hydroxy-2-(4-hydroxyphenyl)-1-methylethyl]amino]ethyl)phenoxy]-2-methylpropionic acid, BRL37344A and CGP-12177A, optionally in form of the pharmaceutically acceptable salts, in form of the hydrates and/or solvates and optionally in the form of the individual optical isomers, mixtures of the individual enantiomers or racemates thereof, for the manufacture of a medicament for the treatment of the overactive bladder syndrome.

Another embodiment of the present invention relates to the use of Flibanserin 1, optionally in form the free base, the pharmacologically acceptable acid addition salts and/or optionally in form of the hydrates and/or solvates thereof, for the manufacture of a medicament for the treatment of overactive bladder syndrome in combination with one or more, preferably one β3 agonist 2d, selected from the group consisting of AD9677/TAK677, CL 316,243, SB 418790, L-796568, BMS-196085, BRL-35135A, CGP12177A, BTA-243, GW 427353. Trecanidine, Zeneca D7114, SR 59119, solabegron, CL616243, 2-[4-(2-[[(1S,2R)-2-hydroxy-2-(4-hydroxyphenyl)-1-methylethyl]amino]ethyl)phenoxy]-2-methylpropionic acid, BRL37344A and CGP-12177A, optionally in form of the pharmaceutically acceptable salts, in form of the hydrates and/or solvates and optionally in the form of the individual optical isomers, mixtures of the individual enantiomers or racemates thereof.

The Examples which follow illustrate the present invention without restricting its scope:

EXAMPLES OF PHARMACEUTICAL FORMULATIONS

| A) | Tablets | per tablet |
|---|---|---|
| | Flibanserin | 100 mg |
| | lactose | 240 mg |
| | corn starch | 340 mg |
| | polyvinylpyrrolidone | 45 mg |
| | magnesium stearate | 15 mg |
| | | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | Flibanserin | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | Flibanserin | 5 mg |
| | corn starch | 41.5 mg |
| | lactose | 30 mg |
| | polyvinylpyrrolidone | 3 mg |
| | magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Flibanserin | 150 mg |
| | Corn starch | 268.5 mg |
| | Magnesium stearate | 1.5 mg |
| | | 420 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | Flibanserin | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion.

| F) | Suppositories | |
|---|---|---|
| | Flibanserin | 50 mg |
| | solid fat | 1650 mg |
| | | 1700 mg |

The hard fat is melted. At 40° C. the ground active substance is homogeneously dispersed. It is cooled to 38° C. and poured into slightly chilled suppository moulds.

G) Film Coated Tablet: Combination of Flibanserin with 2a

Core

| Constituents | mg/tablet |
|---|---|
| Flibanserin | 50.000 |
| Tolterodine | 70.225 |
| Anhydrous dibasic calcium phosphate | 100.000 |
| Microcrystalline cellulose | 203.090 |
| HPMC (Methocel E5) | 6.615 |
| Croscarmellose sodium | 8.820 |
| Magnesium stearate | 2.250 |

Coating

| Constituents | mg/tablet |
|---|---|
| HPMC (Methocel E5) | 4.320 |
| Polyethylene Glycol 6000 | 1.260 |
| Titanium dioxide | 1.800 |
| Talc | 1.542 |
| Iron oxide red | 0.078 |
| Total Film coated tablet | 450.000 |

H) Film Coated Tablet: Combination of Flibanserin with 2b

Core

| Constituents | mg/tablet |
|---|---|
| Flibanserin | 50.000 |
| Desmopressin | 10.000 |
| Lactose monohydrate | 133.750 |
| Microcrystalline cellulose | 40.000 |
| Hydroxypropylcellulose | 2.500 |
| Corn starch | 12.500 |
| Magnesium stearate | 1.250 |

Coating

| Constituents | mg/tablet |
|---|---|
| HPMC (e.g. Pharmacoat 606) | 2.400 |
| Polyethylene Glycol 6000 | 0.700 |
| Titanium dioxide | 1.000 |
| Talc | 0.857 |
| Iron oxide yellow | 0.043 |
| Total Film coated tablet | 255.000 |

I) Film Coated Bilayer Tablet: Combination of Flibanserin with 2c

Core

| Constituents | mg/tablet |
|---|---|
| Flibanserin | 50.000 |
| Duloxetine | 24.000 |
| Lactose monohydrate | 143.490 |
| Microcrystalline cellulose | 47.810 |
| HPMC (e.g. Pharmacoat 606) | 2.500 |
| Carboxymethylcellulose sodium | 5.000 |
| Mannitol | 60.000 |
| Corn starch | 36.500 |
| Povidone | 1.000 |
| Colloidal silicon dioxide | 1.000 |
| Magnesium stearate | 1.700 |

Coating

| Constituents | mg/tablet |
|---|---|
| HPMC (e.g. Methocel E5) | 3.360 |
| Polyethylene Glycol 6000 | 0.980 |
| Titanium dioxide | 1.400 |
| Talc | 1.200 |
| Iron oxide red | 0.060 |
| Total Film coated bilayer tablet | 380.000 |

The invention claimed is:

1. A method for treating or preventing urinary incontinence comprising administering a therapeutically effective amount of Flibanserin 1, or a pharmacologically acceptable acid addition salt hydrate, or solvate thereof.

2. The method for treating or preventing urinary incontinence according to claim 1, further comprising administering and an active ingredient 2, or a pharmaceutically acceptable salts, hydrate, or solvate thereof.

3. The method for treating or preventing urinary incontinence according to claim 1, wherein the urinary incontinence is overactive bladder syndrome.

4. The method for treating or preventing urinary incontinence according to claim 2, wherein the urinary incontinence is overactive bladder syndrome.

5. The method for treating or preventing urinary incontinence according to claim 1, wherein the urinary incontinence is urgency.

6. The method for treating or preventing urinary incontinence according to claim 1, wherein the urinary incontinence is urge urinary incontinence.

7. The method for treating or preventing urinary incontinence according to claim 1, wherein the urinary incontinence is stress urinary incontinence.

8. The method for treating or preventing urinary incontinence according to claim 1, wherein the urinary incontinence is mixed urinary incontinence.

9. The method for treating or preventing urinary incontinence according to claim 2, wherein the active ingredient 2 is an antimuscarinic agent 2a, vasopressin agonist 2b, Serotonin/Noradrenaline modulator 2c, or β3 agonist 2d.

10. The method for treating or preventing urinary incontinence according to claim 9, wherein the active ingredient 2 is an antimuscarinic agent 2a.

11. The method for treating or preventing minary incontinence according to claim 10, wherein the antimuscarinic agent 2a is Tolterodine, Oxybutynin, Darifenacin, Propiverine, Solifenacin, or Trospium, or a pharmaceutically acceptable acid addition salts, hydrates or solvate thereof.

12. The method for treating or preventing urinary incontinence according to claim 9, wherein the active ingredient 2 is a vasopressin agonist 2b.

13. The method for treating or preventing urinary incontinence according to claim 12, wherein the vasopressin agonists 2b is desmopressin, a pharmaceutically acceptable acid addition salt, hydrate, and/or solvate thereof.

14. The method for treating or preventing urinary incontinence according to claim 9, wherein the active ingredient 2 is a Serotonin/Noradrenaline modulator 2c.

15. The method for treating or preventing urinary incontinence according to claim 14, wherein the Serotonin/Noradrenaline modulator 2c is Venlafaxine, Duloxetine, Reboxetine, or Cizoliritine, or a pharmaceutically acceptable acid addition salts, hydrate, or solvate thereof.

16. The method for treating or preventing urinary incontinence according to claim 9, wherein the active ingredient 2 is a β3 agonist 2d.

17. The method for treating or preventing urinary incontinence according to claim 16, wherein the β3 agonist 2d is AD9677/TAK677, CL 316,243, SB 418790, L-796568, BMS-196085, BRL-35135A, CGP12177A, BTA-243, GW 427353, Trecanidine, Zeneca D7114, SR 59119, solabegron, CL616243, 2-[4-(2-[[(1S,2R)-2-hydroxy-2-(4-hydroxyphenyl)-1-methylethyl]amino]ethyl)phenoxy]-2-methylpropionic acid, BRL37344A, or CGP-12177A, or a pharmaceutically acceptable acid addition salt, hydrate, or solvate thereof.

\* \* \* \* \*